United States Patent
Panousis et al.

(10) Patent No.: US 11,174,321 B2
(45) Date of Patent: Nov. 16, 2021

(54) METHOD OF TREATING ATHEROSCLEROSIS

(71) Applicant: CSL LIMITED, Parkville (AU)

(72) Inventors: Con Panousis, Bundoora (AU);
Karlheinz Peter, Hawthorn East (AU);
Hamid Hosseini, Glen Waverley (AU);
Yung-Chih Chen, Boxhill South (AU)

(73) Assignee: CSL LIMITED, Parkville (AU)

( * ) Notice: Subject to any disclaimer, the term of this patent is extended or adjusted under 35 U.S.C. 154(b) by 191 days.

(21) Appl. No.: 16/090,861

(22) PCT Filed: Apr. 6, 2017

(86) PCT No.: PCT/AU2017/050297
§ 371 (c)(1),
(2) Date: Oct. 3, 2018

(87) PCT Pub. No.: WO2017/173494
PCT Pub. Date: Oct. 12, 2017

(65) Prior Publication Data
US 2019/0309089 A1 Oct. 10, 2019

(30) Foreign Application Priority Data
Apr. 6, 2016 (EP) .................................... 16164009

(51) Int. Cl.
| | | |
|---|---|---|
| *C07K 16/36* | (2006.01) | |
| *A61K 47/60* | (2017.01) | |
| *A61P 9/10* | (2006.01) | |
| *A61K 38/57* | (2006.01) | |
| *C07K 14/765* | (2006.01) | |
| *C07K 14/81* | (2006.01) | |
| *C07K 14/435* | (2006.01) | |
| *C07K 14/47* | (2006.01) | |
| *C12N 9/64* | (2006.01) | |
| *A61K 39/00* | (2006.01) | |

(52) U.S. Cl.
CPC .............. *C07K 16/36* (2013.01); *A61K 38/57* (2013.01); *A61K 47/60* (2017.08); *A61P 9/10* (2018.01); *C07K 14/43568* (2013.01); *C07K 14/4703* (2013.01); *C07K 14/765* (2013.01); *C07K 14/81* (2013.01); *C07K 14/811* (2013.01); *C07K 14/8135* (2013.01); *C12N 9/6424* (2013.01); *A61K 2039/505* (2013.01); *A61K 2039/54* (2013.01); *A61K 2039/545* (2013.01); *C07K 2317/565* (2013.01); *C07K 2317/76* (2013.01); *C07K 2319/00* (2013.01); *C07K 2319/30* (2013.01); *C07K 2319/31* (2013.01)

(58) Field of Classification Search
None
See application file for complete search history.

(56) References Cited

U.S. PATENT DOCUMENTS

| | | | |
|---|---|---|---|
| 4,963,657 A * | 10/1990 | Pixley | C07K 16/40 424/145.1 |
| 5,252,714 A | 10/1993 | Harris et al. | |
| 6,403,077 B1 | 6/2002 | Strom et al. | |
| 8,119,137 B2 * | 2/2012 | Nieswandt | A61P 7/10 424/145.1 |
| 9,856,326 B2 * | 1/2018 | Panousis | A61P 27/02 |
| 2004/0087778 A1 | 5/2004 | Feige et al. | |
| 2008/0254039 A1 * | 10/2008 | Nieswandt | A61P 29/00 424/158.1 |
| 2009/0304685 A1 * | 12/2009 | Pritchard | C07K 16/36 424/133.1 |

FOREIGN PATENT DOCUMENTS

| | | | | |
|---|---|---|---|---|
| EP | 0 154 316 A2 | 9/1985 | | |
| EP | 0 401 384 A1 | 12/1990 | | |
| EP | 2 623 110 A1 | 8/2013 | | |
| WO | WO 92/16221 A1 | 10/1992 | | |
| WO | WO 95/34326 A1 | 12/1995 | | |
| WO | WO 01/79271 A1 | 10/2001 | | |
| WO | WO-0179271 A1 * | 10/2001 | ............. | A61P 15/10 |
| WO | WO 03/076567 A2 | 9/2003 | | |
| WO | WO 2004/101740 A2 | 11/2004 | | |
| WO | WO 2005/000892 A2 | 1/2005 | | |
| WO | WO 2005/001025 A2 | 1/2005 | | |
| WO | WO 2005/024044 A2 | 3/2005 | | |
| WO | WO 2005/063808 A1 | 7/2005 | | |
| WO | WO 2006/033386 A1 | 3/2006 | | |
| WO | WO 2006/066878 A1 | 6/2006 | | |
| WO | WO 2008/098720 A1 | 8/2008 | | |
| WO | WO 2010/080538 A1 | 7/2010 | | |
| WO | WO 2012/158003 A1 | 11/2012 | | |
| WO | WO 2013/014092 A1 | 1/2013 | | |
| WO | WO-2013014092 A1 * | 1/2013 | ............. | A61P 31/04 |
| WO | WO 2014/135694 A1 | 9/2014 | | |
| WO | WO 2014/207199 A1 | 12/2014 | | |
| WO | WO 2015/193457 A1 | 12/2015 | | |

OTHER PUBLICATIONS

Janeway et al., Immunobiology, 3rd edition, 1997 Garland Publishing Inc., pp. 3:1-3:11.*
Rudikoff et al., Proc Natl Acad Sci USA. Mar. 1982;79(6):1979-83.*
Al-Lazikani et al., "Standard Conformations for the Canonical Structures of Immunoglobulins," *J. Mol. Biol.*, 273: 927-948 (1997).
Beattie et al., "Structure and evolution of human α-fetoprotein deduced from a partial sequence of cloned cDNA," *Gene*, 20: 415-422 (1982).

(Continued)

*Primary Examiner* — Michael Szperka
(74) *Attorney, Agent, or Firm* — Finnegan, Henderson, Farabow, Garrett & Dunner LLP

(57) ABSTRACT

The present disclosure relates to a method of treating or preventing atherosclerosis in a subject by administering an inhibitor of FXII.

13 Claims, 5 Drawing Sheets

Specification includes a Sequence Listing.

(56) References Cited

OTHER PUBLICATIONS

Borissoff et al., "Early Atherosclerosis Exhibits an Enhanced Procoagulant State," *Circulation*, 122(8): 821-830 (2010).
Bork et al., "The Immunoglobulin Fold, Structural Classification, Sequence Patterns and Common Core," *J. Mol. Biol.*, 242: 309-320 (1994).
Campos et al., "Identification and characterization of a novel factor XIIa inhibitor in the hematophagous insect, *Triatoma infestans* (*Hemiptera: Reduviidae*)," *FEBS Letters*, 577: 512-516 (2004).
Campos et al., "Infestin, a thrombin inhibitor presents in Triatoma infestans midgut, a Chagas' disease vector: gene cloning, expression and characterization of the inhibitor," *Insect Biochemistry and Molecular Biology*, 32: 991-997 (2002).
Chothia et al., "Canonical Structures for the Hypervariable Regions of Immunoglobulins," *J. Mol. Biol.*, 196: 901-917 (1987).
Chothia et al., "Conformations of immunoglobulin hypervariable regions," *Nature*, 342: 877-883 (1989).
Cooke et al., "Serum Vitamin D-binding Protein is a Third Member of the Albumin and Alpha Fetoprotein Gene Family," *J. Clin. Invest.*, 76(6): 2420-2424 (1985).
Devereux, et al., "A comprehensive set of sequence analysis programs for the VAX," *Nucleic Acids Research*, 12(1): 387-395 (1984).
Edelman et al., "The Covalent Structure of an Entire γG Immunoglobulin Molecule," *Proc Natl Acad Sci U S A*, 63: 78-85 (1969).
European Search Report, issued in European Patent Application No. 16164009.9, dated Aug. 11, 2016, 7 pages.
Francis, Gillian E., "Protein modification and fusion proteins," *Focus on Growth Factors*, 3(2): 4-10 (1992).
Ganor et al., "Factor XI Deficiency Protects Against Atherogenesis in Apolipoprotein E/Factor XI Double Knockout Mice," *Arterioscler. Thromb. Vasc. Biol.*, 36(3): 475-481 (2016).
Hagedorn et al., "Factor XIIa Inhibitor Recombinant Human Albumin Infestin-4 Abolishes Occlusive Arterial Thrombus Formation Without Affecting Bleeding," *Circulation*, 121: 1510-1517 (2010).
Honegger et al., "Yet Another Numbering Scheme for Immunoglobulin Variable Domains: An Automatic Modeling and Analysis Tool," *J. Mol. Biol.*, 309: 657-670 (2001).
International search report and the written opinion of the international search authority, issued in International Patent Application No. PCT/AU2017/050297, dated May 30, 2017, 14 pages.
Koch, "Role of Coagulation Factor XII in Atherosclerosis," Doctoral Thesis for a doctoral degree at the Graduate School of Life Sciences Julius-Maximilians-Universität Würzburg, 156 pages (2014).
Kuijpers et al., "Factor XII Regulates the Pathological Process of Thrombus Formation on Ruptured Plaques," *Arterioscler. Thromb. Vasc. Biol.*, 34: 1674-1680 (2014).
Laskowski et al., "Protein Inhibitors of Proteinases," *Ann. Rev. Biochem.*, 49: 593-626 (1980).
Lefranc et al., "IMGT unique numbering for immunoglobulin and T cell receptor variable domains and Ig superfamily V-like domains," *Developmental and Comparative Immunology*, 27: 55-77 (2003).
Lichenstein et al., "Afamin Is a New Member of the Albumin α-Fetoprotein, and Vitamin D-binding Protein Gene Family," *The Journal of Biological Chemistry*, 269(27): 18149-18154 (1994).
Malik et al., "Polyethylene Glycol (PEG)-modified Granulocyte-Macrophage Colony-stimulating Factor (GM-CSF) with Conserved Biological Activity," *Exp. Hematol.*, 20: 1028-1035 (1992).
Nahrendorf et al., "Activatable Magnetic Resonance Imaging Agent Reports Myeloperoxidase Activity in Healing Infarcts and Noninvasively Detects the Antiinflammatory Effects of Atorvastatin on Ischemia-Reperfusion Injury," *Circulation*, 117: 1153-1160 (2008).
Ravon et al., "Monoclonal Antibody F1 Binds To the Kringle Domain of Factor XII and Induces Enhanced Susceptibility for Cleavage by Kallikrein," *Blood*, 86(11): 4134-4143 (1995).
Vorlova et al., "Coagulation factor XII induces pro-inflammatory cytokine responses in macrophages and promotes atherosclerosis in mice," *Thrombosis and Haemostasis*, 117(1): 176-187 (2017).
Supplementary European Search Report issued in EP Application No. 17778478.2, dated Jan. 16, 2020, 9 pages.

\* cited by examiner

METHOD OF TREATING ATHEROSCLEROSIS

CROSS-REFERENCE TO RELATED APPLICATIONS

This application is the United States national stage entry under 35 U.S.C. § 371 of International Application No. PCT/AU2017/050297, filed on Apr. 6, 2017 and published as WO 2017/173494 A1, which claims priority to European Patent Application No. 16164009.9, filed on Apr. 6, 2016. The contents of these applications are each incorporated herein by reference in their entirety.

FIELD

The present disclosure relates to a method of treating or preventing atherosclerosis in a subject.

INTRODUCTION

Atherosclerosis is a major health burden in developed countries and is the leading cause of mortality and morbidity worldwide and represents a major economic burden to health care systems. Epidemic proportions of obesity and diabetes mellitus have considerably increased the numbers of atherosclerosis-associated complications, such as myocardial infarction (MI) and stroke.

Atherosclerosis is a chronic inflammatory disease with specific, localized manifestations at the arterial wall. The development of atherosclerosis is driven by inflammatory processes involving a plethora of cells and factors belonging to the innate and/or adaptive immune system.

The role of inflammation in the development of atherosclerosis has been studied. For example, blood leukocytes, mediators of host defences and inflammation, localize in the earliest lesions of atherosclerosis. Elevation of inflammatory markers has been shown to predict outcome of patients with acute coronary syndromes, independently of myocardial damage. In addition, low-grade chronic inflammation, as indicated by levels of the inflammatory marker C-reactive protein, has been shown to correlate with risk of atherosclerotic complications.

Atherosclerotic lesions, or atherosclerotic plaques, are separated into two broad categories: stable and unstable (also called vulnerable). Typically, stable atherosclerotic plaques, which tend to be asymptomatic, are rich in extracellular matrix and smooth muscle cells, whilst unstable plaques are rich in macrophages and foam cells, and are usually fragile and prone to rupture. Instability of atherosclerotic plaques is driven by inflammatory processes. Atherosclerotic plaques can become unstable and rupture without warning, resulting in the formation of an occlusive arterial thrombus. Ruptured plaques are heavily infiltrated by inflammatory cells, such as macrophages, which secrete proteolytic enzymes including plasminogen activators, cathepsins and matrix metalloproteinases, and fibrotic tissue. Ruptured atherosclerotic plaques manifest clinically as myocardial infarction and stroke. As a consequence, many patients suffer a sudden cardiac death or fatal stroke.

The most common treatment options for atherosclerotic lesions include administration of lipid-lowering drugs such as statins (e.g., Lovastatin, Pravastatin, Rosuvastatin, Simvastatin, Atorvastatin, and Fluvastatin) and blood-thinning drugs (anticoagulants like e.g., Aspirin, Clopidogrel, Prasugrel, Ticagrelor, Warfarin and Heparin). However, on-going use of the latter therapeutics increases the risk of dangerous bleeding.

The role of clotting factors in atherosclerosis has also been studied. For example, Schnerb et al., (Arterioscler Thromb Vasc Biol., 36: 475-481, 2016) studied atherosclerosis development in mice lacking apolipoprotein E and Factor XI (FXI). The authors found atherogenesis was slowed in FXI deficient mice. However, these studies are based on animals that have lacked FXI since birth and do not study the effects of inhibiting the protein following or during development of atherosclerosis.

Therefore, there is a need in the art for improved treatments for atherosclerosis and its thrombotic complications.

SUMMARY

In producing the present invention, the inventors studied the effects of inhibiting Factor XII (FXII) in mouse models of atherosclerosis, e.g., atherosclerotic plaque formation and/or atherosclerotic plaque instability and rupture. The inventors studied the effects of FXII inhibition based on their understanding that this protein has effects on numerous biological pathways, some of which may be involved in atherosclerosis, e.g., inflammation. The inventors found that inhibition of FXII not only slows progression of atherosclerosis, but also attenuates development of atherosclerotic lesions, reduces lesion size and stabilizes unstable atherosclerotic plaques as evidenced by a reduction in inflammatory cell accumulation in the lesion, increase in collagen deposition and reduction in necrotic core area. The inventors demonstrated these effects by administering an inhibitor of FXII to accepted animal models of atherosclerosis, i.e., that mimic the situation observed in humans. The experimental evidence includes the findings that FXII inhibitors are useful in the treatment and/or prevention of atherosclerosis by attenuating the progression and development of atherosclerotic legions, reducing arterial inflammation and stabilizing plaques.

The findings by the inventors provide the basis for methods for treating or preventing atherosclerosis in a subject by inhibiting FXII. The findings by the inventors also provide the basis for or an inhibitor of FXII for use in treating or preventing atherosclerosis in a subject.

In other words, the inventors provide the basis for or an inhibitor of Factor XII for use in treating or preventing atherosclerosis in a subject by (i) preventing atherosclerotic plaques formation in a subject and/or (ii) stabilizing vulnerable atherosclerotic plaques in a subject and/or (iii) preventing atherosclerotic plaque rupture in a subject.

For example, the present disclosure provides a method for treating atherosclerosis in a subject comprising administering to the subject an inhibitor of FXII. In another example, the disclosure provides a method for preventing atherosclerosis in a subject, the method comprising administering to the subject an inhibitor of FXII.

In an alternative example, the present disclosure provides an inhibitor of FXII for use in treating atherosclerosis in a subject. In another example, the disclosure provides an inhibitor of FXII for use in preventing atherosclerosis in a subject.

The inventors have also found that they can reduce the progression of atherosclerotic lesions in a subject. Accordingly, the present disclosure additionally provides a method for or an inhibitor of FXII for use in reducing the progression of atherosclerosis in a subject. For example, the present disclosure provides a method for or an inhibitor of FXII for use in reducing the risk of or preventing atherosclerotic plaque rupture in a subject. In one example, the present disclosure provides a method for or an inhibitor of FXII for use in stabilization of unstable atherosclerotic plaques. In one example, the present disclosure provides a method for or an inhibitor of FXII for use in preventing atherosclerotic plaques formation.

In one example, the inhibitor of FXII is a direct inhibitor. In one example, the inhibitor of FXII binds to FXII and/or FXIIa. In one example, the inhibitor of FXII binds to FXII and/or FXIIa and inhibits the activity of FXII and/or FXIIa. For example, the inhibitor of FXII binds to FXIIa and inhibits the activity of FXIIa. In another example, the inhibitor of FXII binds to FXII and inhibits FXII activation. In one example, the activity of FXII and/or FXIIa is inhibited by at least about 50%. For example, the activity of FXII and/or FXIIa is inhibited by about 60%, or about 70%, or about 80%, or about 85%, or about 90%, or about 95%, or about 99%, or about 100%. Methods for determining the activity of FXII and/or FXIIa are known in the art and/or described herein.

In one example, the inhibitor of FXII is a serine protease inhibitor. For example, the FXII inhibitor is Infestin-4. In another example, the FXII inhibitor is SPINK-1. In a further example, the FXII inhibitor is an Infestin-4 or SPINK-1 variant.

In one example, the inhibitor of FXII is not a serine protease inhibitor. For example, the inhibitor of FXII is not Infestin-4. For example, the inhibitor of FXII is not a variant of Infestin-4. In one example, the inhibitor of FXII is not SPINK-1. For example, the inhibitor of FXII is not a variant of SPINK-1.

In one example, the method of or the inhibitor of FXII for use in the present disclosure comprises administering an inhibitor of FXII, wherein the inhibitor comprises:
(i) the wild type Infestin-4 polypeptide sequence (SEQ ID NO: 1), or a polypeptide sequence comprising:
  (a) SEQ ID NO: 1 modified to contain 1-5 amino acid mutations outside of N-terminal amino acid positions 2-13 of SEQ ID NO: 1; and/or
  (b) an identity of at least 70% to SEQ ID NO: 1 and retaining six conserved cysteine residues from SEQ ID NO: 1; or
(ii) a wild-type SPINK-1 polypeptide sequence (SEQ ID NO: 2), or a polypeptide sequence comprising:
  (a) SEQ ID NO: 2 mutated to replace N-terminal amino acid positions 2-13 with the N-terminal amino acids 2-13 of SEQ ID NO: 1; and optionally further modified to contain 1-5 additional amino acid mutations that increase the homology of the polypeptide sequence to sequence of SEQ ID NO: 1; and/or
  (b) an identity of at least 70% to SEQ ID NO: 2 and retaining six conserved cysteine residues from SEQ ID NO: 2; and/or
(iii) one of SPINK-1 mutants K1 (SEQ ID NO: 3), K2 (SEQ ID NO: 4), or K3 (SEQ ID NO: 5).

In one example, the inhibitor of FXII comprises the sequence of the serine protease inhibitor Infestin-4. For example, the inhibitor of FXII comprises the sequence set forth in SEQ ID NO: 1.

In one example, the inhibitor of FXII comprises a modified Infestin-4. For example, the inhibitor of FXII comprises the sequence set forth in SEQ ID NO: 1 modified to contain 1-5 amino acid mutations outside of N-terminal amino acid positions 2-13 of SEQ ID NO: 1.

In another example, the inhibitor of FXII comprises a sequence with at least 70% identity to the sequence set forth in SEQ ID NO: 1 and retaining six conserved cysteine residues from SEQ ID NO: 1. For example, the inhibitor of FXII has an identity of about 75% to SEQ ID NO: 1, or an identity of about 80% to SEQ ID NO: 1, or an identity of about 85% to SEQ ID NO: 1, or an identity of about 90% to SEQ ID NO: 1, or an identity of about 95% to SEQ ID NO: 1, or an identity of about 98% to SEQ ID NO: 1, or an identity of about 99% to SEQ ID NO: 1.

In one example, the inhibitor of FXII comprises the sequence of the serine protease inhibitor SPINK-1. For example, the inhibitor of FXII comprises the sequence set forth in SEQ ID NO: 2.

In another example, the inhibitor of FXII comprises the sequence set forth in SEQ ID NO: 2 mutated to replace N-terminal amino acid positions 2-13 with the N-terminal amino acids 2-13 of SEQ ID NO: 1; and optionally further modified to contain 1-5 additional amino acid mutations that increase the homology of the polypeptide sequence to sequence of SEQ ID NO: 1.

In another example, the inhibitor of FXII comprises a sequence with at least 70% identity to the sequence set forth in SEQ ID NO: 2 and retaining six conserved cysteine residues from SEQ ID NO: 2. For example, the inhibitor of FXII has an identity of about 75% to SEQ ID NO: 2, or an identity of about 80% to SEQ ID NO: 2, or an identity of about 85% to SEQ ID NO: 2, or an identity of about 90% to SEQ ID NO: 2, or an identity of about 95% to SEQ ID NO: 2, or an identity of about 98% to SEQ ID NO: 2, or an identity of about 99% to SEQ ID NO: 2.

In one example, inhibitor of FXII is a protein comprising a variable region fragment (Fv). For example, the protein is selected from the group consisting of:
(i) a single chain Fv fragment (scFv);
(ii) a dimeric scFv (di-scFv); or
(iii) a diabody;
(iv) a triabody;
(v) a tetrabody;
(vi) a Fab;
(vii) a F(ab')2;
(viii) a Fv;
(ix) one of (i) to (ix) linked to a constant region of an antibody, Fc or a heavy chain constant domain ($C_H$) 2 and/or $C_H3$; or
(x) an antibody.

In one example, an inhibitor of FXII is an antibody. For example, the antibody is an anti-FXII antibody. In another example, the antibody is an anti-FXIIa antibody.

Exemplary antibodies are full-length and/or naked antibodies.

In one example, the inhibitor of FXII is a protein that is recombinant, chimeric, CDR grafted, humanized, synhumanized, primatized, deimmunized or human.

In one example, the antibody is an IgG antibody.

In one example, the anti-FXII antibody comprises a heavy chain variable region ($V_H$) comprising a sequence set forth in SEQ ID NO: 6.

In one example, the anti-FXII antibody comprises a light chain variable region ($V_L$) comprising a sequence set forth in SEQ ID NO: 7.

In one example, the anti-FXII antibody comprises a $V_H$ comprising a sequence set forth in SEQ ID NO: 6 and a $V_L$ comprising a sequence set forth in SEQ ID NO: 7.

In one example, the anti-FXII antibody comprises a variable region comprising the complementary determining regions (CDRs) of the $V_H$ and/or the $V_L$ of SEQ ID NO: 6 and SEQ ID NO: 7.

In one example, the protein or antibody is any form of the protein or antibody encoded by a nucleic acid encoding any of the foregoing proteins or antibodies, such as a variant missing an encoded C-terminal lysine residue, a deamidated variant and/or a glycosylated variant and/or a variant comprising a pyroglutamate, e.g., at the N-terminus of a protein and/or a variant lacking a N-terminal residue.

In one example, the anti-FXII antibody comprises:
(i) a $V_H$ comprising:
  (a) a sequence set forth in SEQ ID NO: 6; or
  (b) a CDR1 comprising a sequence set forth in SEQ ID NO: 8; a CDR2 comprising a sequence set forth in SEQ ID NO: 10; and a CDR3 comprising a sequence set forth in SEQ ID NO: 12; or
  (c) a CDR1 comprising a sequence set forth in SEQ ID NO: 8; a CDR2 comprising a sequence set forth in SEQ ID NO: 9; and a CDR3 comprising a sequence set forth in SEQ ID NO: 11; and/or
(ii) a $V_L$ comprising:
  (a) a sequence set forth in SEQ ID NO: 7; or
  (b) a CDR1 comprising a sequence set forth in SEQ ID NO: 13; a CDR2 comprising a sequence set forth in SEQ ID NO: 14; and a CDR3 comprising a sequence set forth in SEQ ID NO: 16; or
  (c) a CDR1 comprising a sequence set forth in SEQ ID NO: 13; a CDR2 comprising a sequence set forth in SEQ ID NO: 14; and a CDR3 comprising a sequence set forth in SEQ ID NO: 15.

In one example, the anti-FXII antibody comprises:
(i) a $V_H$ comprising:
  (a) a CDR1 comprising a sequence set forth in SEQ ID NO: 8;
  (b) a CDR2 comprising a sequence set forth in SEQ ID NO: 10; and
  (c) a CDR3 comprising a sequence set forth in SEQ ID NO: 12; and/or
(ii) a $V_L$ comprising:
  (a) a CDR1 comprising a sequence as set forth in SEQ ID NO: 13;
  (b) a CDR2 comprising a sequence as set forth in SEQ ID NO: 14; and
  (c) a CDR3 comprising a sequence as set forth in SEQ ID NO: 16.

In one example, the anti-FXII antibody comprises:
(i) a $V_H$ comprising:
  (a) a CDR1 comprising a sequence set forth in SEQ ID NO: 8;
  (b) a CDR2 comprising a sequence set forth in SEQ ID NO: 9; and
  (c) a CDR3 comprising a sequence set forth in SEQ ID NO: 11; and/or
(ii) a $V_L$ comprising:
  (a) a CDR1 comprising a sequence as set forth in SEQ ID NO: 13;
  (b) a CDR2 comprising a sequence as set forth in SEQ ID NO: 14; and
  (c) a CDR3 comprising a sequence as set forth in SEQ ID NO: 15.

In one example, the anti-FXII antibody comprises:
(i) a $V_H$ comprising
  (a) a CDR1 set forth in SEQ ID NO: 8;
  (b) a CDR2 set forth in SEQ ID NO: 10 wherein the X at position 3 is D, the X at position 4 is I, the X at position 5 is P, the X at position 6 is T, the X at position 7 is K, and the X at position 8 is G; and
  (c) a CDR3 set forth in SEQ ID NO: 11; and/or
(ii) a $V_L$ comprising
  (a) a CDR1 set forth in SEQ ID NO: 13;
  (b) CDR2 set forth in SEQ ID NO: 14; and
  (c) a CDR3 set forth in SEQ ID NO: 15.

For example, the anti-FXII antibody comprises a $V_H$ comprising a sequence set forth in SEQ ID NO: 18 and a $V_L$ comprising a sequence set forth in SEQ ID NO: 19.

In one example, the anti-FXII antibody comprises lambda light chain constant regions.

In one example, the anti-FXII antibody comprises IgG4 or stabilized IgG4 constant regions. For example, the stabilized IgG4 constant regions comprise a proline at position 241 of the hinge region according to the system of Kabat (Kabat et al., Sequences of Proteins of Immunological Interest Washington D.C. United States Department of Health and Human Services, 1987 and/or 1991).

In one example, the anti-FXII antibody comprises a heavy chain comprising a sequence set forth in SEQ ID NO: 20 and a light chain comprising a sequence set forth in SEQ ID NO: 21.

In one example, the anti-FXII antibody is within a composition. For example, the composition comprises a protein comprising an antibody variable region or a $V_H$ or a $V_L$ or an antibody as described herein. In one example, the composition additionally comprises one or more variants of the protein or antibody. For example, that comprises a variant missing an encoded C-terminal lysine residue, a deamidated variant and/or a glycosylated variant and/or a variant comprising a pyroglutamate, e.g., at the N-terminus of a protein and/or a variant lacking a N-terminal residue, e.g., a N-terminal glutamine in an antibody or V region and/or a variant comprising all or part of a secretion signal. Deamidated variants of encoded asparagine residues may result in isoaspartic, and aspartic acid isoforms being generated or even a succinamide involving an adjacent amino acid residue. Deamidated variants of encoded glutamine residues may result in glutamic acid. Compositions comprising a heterogeneous mixture of such sequences and variants are intended to be included when reference is made to a particular amino acid sequence.

In one example, of any method or an inhibitor of FXII for use described herein, the inhibitor of FXII is linked to a fusion partner. For example, the fusion partner comprises polyethylene glycol (PEG) or a half-life enhancing polypeptide.

In one example, the inhibitor of FXII is linked to the fusion partner directly. In another example, the inhibitor of FXII is linked to the fusion partner via a linker. For example, the inhibitor of FXII is linked to a half-life enhancing polypeptide directly. In another example, the inhibitor of FXII is linked to a half-life enhancing polypeptide via a linker. In one example, the inhibitor of FXII is linked to the PEG directly. In another example, the inhibitor of FXII is linked to the PEG via a linker.

In one example, the linker is an intervening peptidic linker. For example, the linker is a cleavable linker.

In one example, the half-life enhancing polypeptide is selected from the group consisting of albumin, afamin, alpha-fetoprotein, vitamin D binding protein, human albumin, an immunoglobulin, and an Fc of an IgG. For example, the half-life enhancing polypeptide is albumin.

In one example, the inhibitor of FXII is a fusion protein comprising human albumin linked to a FXII inhibitor via a linker peptide.

In one example, the inhibitor of FXII is administered parenterally. For example, the inhibitor of FXII is administered intravenously, or subcutaneously, or intrathecal. In one example, the inhibitor of FXII is administered subcutaneously. In another example, the inhibitor of FXII is administered intravenously.

In one example of any method described herein, the inhibitor of FXII is administered to the subject in one or more doses. For example, the inhibitor of FXII is administered to the subject:
(i) in a single dose; or
(ii) in a plurality of doses; or
(iii) as a continuous infusion or application.

In one example, the inhibitor of FXII is administered to the subject in a single dose.

In one example, the inhibitor of FXII is administered to the subject in a plurality of doses. For example, the inhibitor of FXII is administered to the subject as two doses, or three doses, or four doses, or five doses or more. For example, administration of each dose of the inhibitor of FXII is separated by a period of hours. For example, administration of each dose of the inhibitor of FXII is separated by the period of about 1 hour, or about 2 hours, or about 3 hours, or about 4 hours, or about 6 hours, or about 8 hours, or about 12 hours, or about 16 hours, or about 20 hours, or about 24 hours.

For example, administration of each dose of the inhibitor of FXII is separated by a period of days. For example, administration of each dose of the inhibitor of FXII is separated by the period of about 1 day, or about 2 days, or about 3 days, or about 4 days or about 5 days, or about 6 days, or about 7 days.

In one example, administration of each dose of the inhibitor of FXII is separated by at least 14 days or at least 28 days.

For example, administration of each dose of the inhibitor of FXII is separated by a period of weeks. For example, administration of each dose of the inhibitor of FXII is separated by the period of about 1 week, or about 2 weeks, or about 3 weeks, or about 4 weeks, or about 5 weeks, or about 6 weeks.

In one example, administration of each dose of the inhibitor of FXII is separated by at least one month.

In one example, the length of time between administrations of the inhibitor of FXII is the same throughout the course of administration. In one example, the length of time between administrations of the inhibitor of FXII is different throughout the course of administration. For example, the inhibitor of FXII is administered on a weekly basis at the commencement of therapy and then on a monthly basis following a predetermined number of doses. In one example, the length of time between administrations of the inhibitor of FXII is variable.

In one example, the inhibitor of FXII is administered to the subject as a continuous dose. For example, the inhibitor of FXII is administered to the subject as a continuous infusion over a period of time. For example, the inhibitor of FXII is administered over a period of between about 1 minute to about 24 hours. For example, the inhibitor of FXII is administered over a period of about 10 minutes to about 12 hours, or about 10 minutes to about 6 hours, or about 10 minutes to about 5 hours, or about 10 minutes to about 4 hours, or about 10 minutes to about 3 hours, or about 10 minutes to about 2 hours, or about 10 minutes to about 1 hour, or about 30 minutes.

In one example, the inhibitor of FXII is administered a plurality of times. For example, the inhibitor of FXII is administered one or more times. For example, the inhibitor of FXII is administered until the atherosclerosis is treated or prevented. For example, the inhibitor of FXII is administered for a period of days to months. For example, the inhibitor of FXII is administered for about one day, or about 2 days, or about 3 days, or about 4 days, or about 5 days, or about 6 days, or about 1 week, or about 2 weeks, or about 4 weeks, or about six weeks, or about 2 months.

In one example, the inhibitor of FXII is administered in a therapeutically or prophylactically effective amount. For example, the inhibitor of FXII is administered to the subject at a dose of about 0.01 mg/kg to about 1000 mg/kg. For example, the inhibitor of FXII is administered at a dose of about 0.01 mg/kg bodyweight, or about 0.1 mg/kg bodyweight, or about 1 mg/kg bodyweight, or about 50 mg/kg bodyweight, or about 100 mg/kg bodyweight, or about 200 mg/kg bodyweight, or about 500 mg/kg bodyweight, or about 1000 mg/kg bodyweight. For example, the inhibitor of FXII is administered at a dose of about 0.001 mg/kg to about 100 mg/kg body weight, or about 0.01 mg/kg to about 100 mg/kg, or about 0.01 mg/kg to about 50 mg/kg, or about 0.1 mg/kg to about 30 mg/kg, or about 0.1 mg/kg to about 10 mg/kg, or about 0.1 mg/kg to about 5 mg/kg, or about 0.1 mg/kg to about 2 mg/kg or about 0.1 mg/kg to about 1 mg/kg. In one example, the inhibitor of FXII is administered at a dose ranging from about 0.01 mg/kg to about 1000 mg/kg, or about 0.1 mg/kg to about 1000 mg/kg, or about 1 mg/kg to about 1000 mg/kg, or about 1 mg/kg to about 500 mg/kg, or about 10 mg/kg to about 200 mg/kg, or about 10 mg/kg to about 100 mg/kg, or about 50 mg/kg to about 500 mg/kg, or about 50 mg/kg to about 200 mg/kg, or about 100 mg/kg to about 200 mg/kg. In one example, the inhibitor of FXII is administered at a dose of about 10 mg/kg. In one example, the inhibitor of FXII is administered at a dose of about 20 mg/kg.

In one example, the subject has atherosclerosis. In one example, the subject has been diagnosed as suffering from atherosclerosis. In one example, the subject is receiving treatment for atherosclerosis. In one example, the subject is receiving treatment for atherosclerosis associated condition (i.e., myocardial infarct). For example, the subject is receiving treatment with a statin or warfarin or a β-blocker or anti-platelet drug.

In one example, the subject has previously suffered a myocardial infarction. In one example the subject is receiving treatment with a statin, warfarin and a β-blocker.

In one example of any method or an inhibitor of FXII for use described herein, the subject is at risk of developing atherosclerosis. In this regard, the inhibitor of FXII is used in a preventative or prophylactic manner or can be said to be used in a primary preventative manner. An exemplary subject at risk of developing atherosclerosis suffers from diabetes and/or obesity. For example, the diabetes is type 2 diabetes.

Additional or alternative characteristics of a subject at risk of suffering from atherosclerosis include one or more of the following characteristics:
  has already suffered from angina, and/or stroke and/or heart attack;
  has peripheral artery disease;
  has a family history of heart disease;
  has high plasma low density lipoprotein levels;
  has low plasma high density lipoprotein levels; and/or
  has high blood pressure.

In one example, a subject at risk of suffering from atherosclerosis has a high plasma low density lipoprotein level. For example, the plasma low density lipoprotein level is at least 160 mg/dL.

In one example, a subject at risk of suffering from atherosclerosis has a low plasma high density lipoprotein level. For example, the plasma high density lipoprotein level is less than about 50 mg/dL.

In one example, a subject at risk of suffering from atherosclerosis has high blood pressure. For example, the blood pressure level is at least 140/90 mmHg.

In one example, the subject is additionally aged 55 years or more, e.g., 65 years or more, or 75 years or more.

In one example, the subject has increased levels of an inflammatory marker. For example, the subject has increased levels of C-reactive protein, e.g., 3-5 mg/L.

In one example of any method described herein, the inhibitor of FXII is administered to the subject before or after the onset of atherosclerosis. For example, the inhibitor of FXII is administered prophylactically or therapeutically. In one example, the inhibitor is administered to the subject prophylactically. In one example, the inhibitor is administered to the subject therapeutically.

In one example of any method or an inhibitor of FXII for use described herein, the atherosclerosis in the subject may result in a myocardial infarct or stroke. For example, atherosclerotic plaque rupture may result in occlusive arterial thrombosis at the site of rupture which clinically manifests as a myocardial infarct or stroke. Accordingly, the present disclosure additionally provides a method for reducing the risk of occlusive arterial thrombosis and/or myocardial infarction and/or stroke by performing a method described herein. In another example, the present disclosure provides a method for preventing occlusive arterial thrombosis and/or myocardial infarction and/or stroke by performing a method described herein.

Methods for assessing each of the foregoing are known in the art and/or described herein.

In one example, the inhibitor of FXII is administered in an amount sufficient to have one or more of the following effects:
(i) reducing the likelihood of occlusive arterial thrombus in a subject;
(ii) reducing atherosclerotic plaque lesion size in a subject;
(iii) increasing plaque stabilization in a subject;
(iv) reducing inflammatory cell accumulation in an atherosclerotic plaque lesion in a subject; and/or
(v) reducing pro-atherogenic cell populations in a subject.

In one example, the inhibitor of FXII is administered in an amount sufficient to stabilize atherosclerotic plaques. For example, lipid accumulation in an atherosclerotic plaque lesion in a subject is reduced. In one example, collagen deposition in an atherosclerotic plaque lesion in a subject is increased. In one example, necrotic core area in an atherosclerotic plaque lesion in a subject is reduced. In one example, smooth muscle cell number in an atherosclerotic plaque lesion in a subject is increased. In another example, the expression of vascular cell adhesion molecule-1 (VCAM-1) in an atherosclerotic plaque lesion in a subject is reduced. Accordingly, the present disclosure provides a method for or an inhibitor of FXII for use in reducing lipid accumulation and/or increasing collagen deposition and/or reducing necrotic core area and/or increasing smooth muscle cell number and/or reducing expression of vascular cell adhesion molecule-1 in an atherosclerotic plaque lesion in a subject by performing a method or an inhibitor of FXII for use described herein. For example, the reduction and/or increase are relative to an atherosclerotic plaque in a subject that is not treated with the inhibitor of FXII. In one example, the reduction and/or increase is relative to an atherosclerotic plaque in a subject prior to the commencement of treatment with an inhibitor of FXII.

In one example, the inhibitor of FXII is administered in an amount sufficient to reduce inflammatory cell accumulation in an atherosclerotic plaque lesion in a subject. For example, macrophage accumulation in an atherosclerotic plaque lesion in a subject is reduced.

In one example, the inhibitor of FXII is administered in an amount sufficient to reduce pro-atherogenic cell populations in the atherosclerotic plaque. For example, circulating natural killer and/or natural killer T cell populations in a plaque are reduced.

In one example of any method described herein, the inhibitor of FXII is administered before or after the development of atherosclerosis. In one example, the inhibitor of FXII is administered before the development of atherosclerosis. In one example, the inhibitor of FXII is administered after the development of atherosclerosis.

In one example, the inhibitor of FXII is administered after the onset of symptoms of atherosclerosis. In one example, the inhibitor of FXII is administered at a dose that alleviates or reduces one or more of the symptoms of atherosclerosis.

Symptoms of atherosclerosis will be apparent to the skilled person and include, for example:
chest pain on exertion or angina;
chest pain at rest;
pain in the arms, shoulder, abdomen, or jaw;
cardiac arrest;
shortness of breath;
being generally unwell;
numbness or weakness in the subject's arm(s) or leg(s);
difficulty speaking or slurred speech;
temporary loss of vision;
drooping muscles in the subject's face; and/or
fatigue.

In one example of any method or an inhibitor of FXII for use described herein, the subject is a mammal, for example a primate, such as a human.

Methods of treatment or inhibitors of FXII for use described herein can additionally comprise administering a further compound to reduce, treat or prevent the effect of atherosclerosis.

The present disclosure also provides a composition comprising an inhibitor of FXII for use in treating or preventing atherosclerosis in a subject in need thereof.

The present disclosure also provides use of an inhibitor of FXII in the manufacture of a medicament for treating or preventing atherosclerosis in a subject.

The present disclosure also provides a kit comprising at least one inhibitor of FXII packaged with instructions for use in treating or preventing atherosclerosis in a subject. Optionally, the kit additionally comprises a therapeutically active compound or drug.

The present disclosure also provides a kit comprising at least one inhibitor of FXII packaged with instructions to administer the inhibitor of FXII to a subject who is suffering from or at risk of suffering from atherosclerosis, optionally, in combination with a therapeutically active compound or drug.

Exemplary effects of atherosclerosis and inhibitors of FXII are described herein and are to be taken to apply mutatis mutandis to the examples of the disclosure set out in the previous five paragraphs.

An inventor has also produced an inhibitor of FXII, e.g., an anti-FXII antibody or antigen binding fragment thereof suitable for use in treating a human subject. This inhibitor is an affinity matured human antibody that has been modified to make most, but not all, residues in the framework regions the same as those in a germline human antibody thereby reducing the potential for immunogenicity. This antibody is also capable of inhibiting FXIIa and has good manufacturability characteristics. Thus, the present disclosure also provides an anti-FXII antibody or antigen binding fragment thereof, wherein the anti-FXII antibody comprises a $V_H$ comprising a sequence set forth in SEQ ID NO: 18 and a $V_L$ comprising a sequence set forth in SEQ ID NO: 19.

In one example, the anti-FXII antibody comprises lambda light chain constant regions.

In one example, the anti-FXII antibody comprises IgG4 or stabilized IgG4 constant regions. For example, the stabilized IgG4 constant regions comprise a proline at position 241 of the hinge region according to the system of Kabat (Kabat et al., Sequences of Proteins of Immunological Interest Washington D.C. United States Department of Health and Human Services, 1987 and/or 1991).

In one example, the anti-FXII antibody comprises a heavy chain comprising a sequence set forth in SEQ ID NO: 20 and a light chain comprising a sequence set forth in SEQ ID NO: 21.

In one example, the disclosure provides a composition comprising the anti-FXII antibody or antigen binding fragment and a carrier, e.g., a pharmaceutically acceptable carrier.

In one example, the composition additionally comprises one or more variants of the protein or antibody. For example, that comprises a variant missing an encoded C-terminal lysine residue, a deamidated variant and/or a glycosylated variant and/or a variant comprising a pyroglutamate, e.g., at the N-terminus of a protein and/or a variant lacking a N-terminal residue, e.g., a N-terminal glutamine in an antibody or V region and/or a variant comprising all or part of a secretion signal. Deamidated variants of encoded asparagine residues may result in isoaspartic, and aspartic acid isoforms being generated or even a succinamide involving an adjacent amino acid residue. Deamidated variants of encoded glutamine residues may result in glutamic acid. Compositions comprising a heterogeneous mixture of such sequences and variants are intended to be included when reference is made to a particular amino acid sequence.

The present disclosure also provides the anti-FXII antibody or antigen binding fragment thereof for medical use.

The present disclosure also provides a method for treating or preventing a disorder in a subject, the method comprising administering the anti-FXII antibody or antigen binding fragment thereof, wherein the disorder is selected from the group consisting of venous, arterial or capillary thrombus formation, thrombus formation in the heart, thrombus formation during and/or after contacting blood of a human or animal subject with artificial surfaces, thromboembolism, by preventing the formation and/or the stabilization of thrombi and thereby three-dimensional intraluminal thrombus growth, or by preventing and/or treating intraluminal thrombi; interstitial lung disease, inflammation, a neurological inflammatory disease, complement activation, fibrinolysis, angiogenesis and diseases related to FXII/FXIIa-induced kinin formation or FXII/FXIIa-mediated complement activation.

The present disclosure also provides a method of treating intraluminal thrombi in a human or animal subject, the method comprising administering an anti-FXII antibody or antigen binding fragment thereof to the subject, wherein the intraluminal thrombi are related to a disorder selected from the group consisting of venous, arterial or capillary thrombus formation, thrombus formation in the heart, thrombus formation during and/or after contacting blood of a human or animal subject with artificial surfaces, thromboembolism; interstitial lung disease, inflammation, a neurological inflammatory disease, complement activation, fibrinolysis, angiogenesis and diseases related to FXII/FXIIa-induced kinin formation or FXII/FXIIa-mediated complement activation. For example, the venous or arterial thrombus formation is stroke, myocardial infarction, deep vein thrombosis, portal vein thrombosis, renal vein thrombosis, jugular vein thrombosis, cerebral venous sinus thrombosis, Budd-Chiari syndrome or Paget-Schroetter disease.

In one example, the diseases related to FXII/FXIIa-induced kinin formation are selected from the group hereditary angioedema, bacterial infections of the lung, trypanosoma infections, hypotensive shock, pancreatitis, chagas disease, articular gout, arthritis, disseminated intravascular coagulation (DIC) and sepsis.

In one example, the interstitial lung disease is fibroproliferative and/or idiopathic pulmonary fibrosis.

In one example, the thrombus formation occurs during and/or after contacting blood of a human or animal subject with artificial surfaces during and/or after a medical procedure performed on said human or animal subject and said antibody or antigen-binding fragment thereof is administered before and/or during and/or after said medical procedure, and further (i) the artificial surface is exposed to at least 80% of the blood volume of the subject and the artificial surface is at least $0.2\ m^2$ or
(ii) the artificial surface is a container for collection of blood outside the body of the subject or
(iii) the artificial surface is a stent, valve, intraluminal catheter, or a system for internal assisted pumping of blood.

The present disclosure also provides a medical device coated with the antibody or antigen-binding fragment thereof of the invention, wherein the device is a cardiopulmonary bypass machine, an extracorporeal membrane oxygenation system for oxygenation of blood, a device for assisted pumping of blood, a blood dialysis device, a device for the extracorporeal filtration of blood, a repository for use in the collection of blood, an intraluminal catheter, a stent, an artificial heart valve, and/or accessories for any one of said devices including tubing, cannulae, centrifugal pump, valve, port, and/or diverter.

The present disclosure also provides a method comprising administering the anti-FXII antibody or antigen binding fragment thereof to a patient receiving a medical procedure, wherein the medical procedure comprises contact with at least one of:
(a) heart,
(b) at least one blood vessel chosen from: the aorta, the aortic arch, a carotid artery, a coronary artery, brachiocephalic artery, vertebrobasilar circulation, intracranial arteries, renal artery, a hepatic artery, a mesenteric artery, and/or a blood vessel of the arterial system cranial to the heart,
(c) a venous blood vessel if the patient has a known septal defect;
and wherein the medical procedure comprises release of at least one embolus in at least one of said blood vessels in the body that could result in ischemia in at least one target organ and administration of the antibody or antigen binding fragment thereof before, during and/or after the medical procedure.

The present disclosure also provides a method for treating or preventing a condition associated with increased vascular permeability, in particular increased retinal vascular permeability, including progressive retinopathy, sight-threatening complication of retinopathy, macular edema, non-proliferative retinopathy, proliferative retinopathy, retinal edema, diabetic retinopathy, hypertensive retinopathy, and retinal trauma, wherein the method comprises administering the anti-FXII antibody or antigen binding fragment thereof.

KEY TO SEQUENCE LISTING

Figure 1:
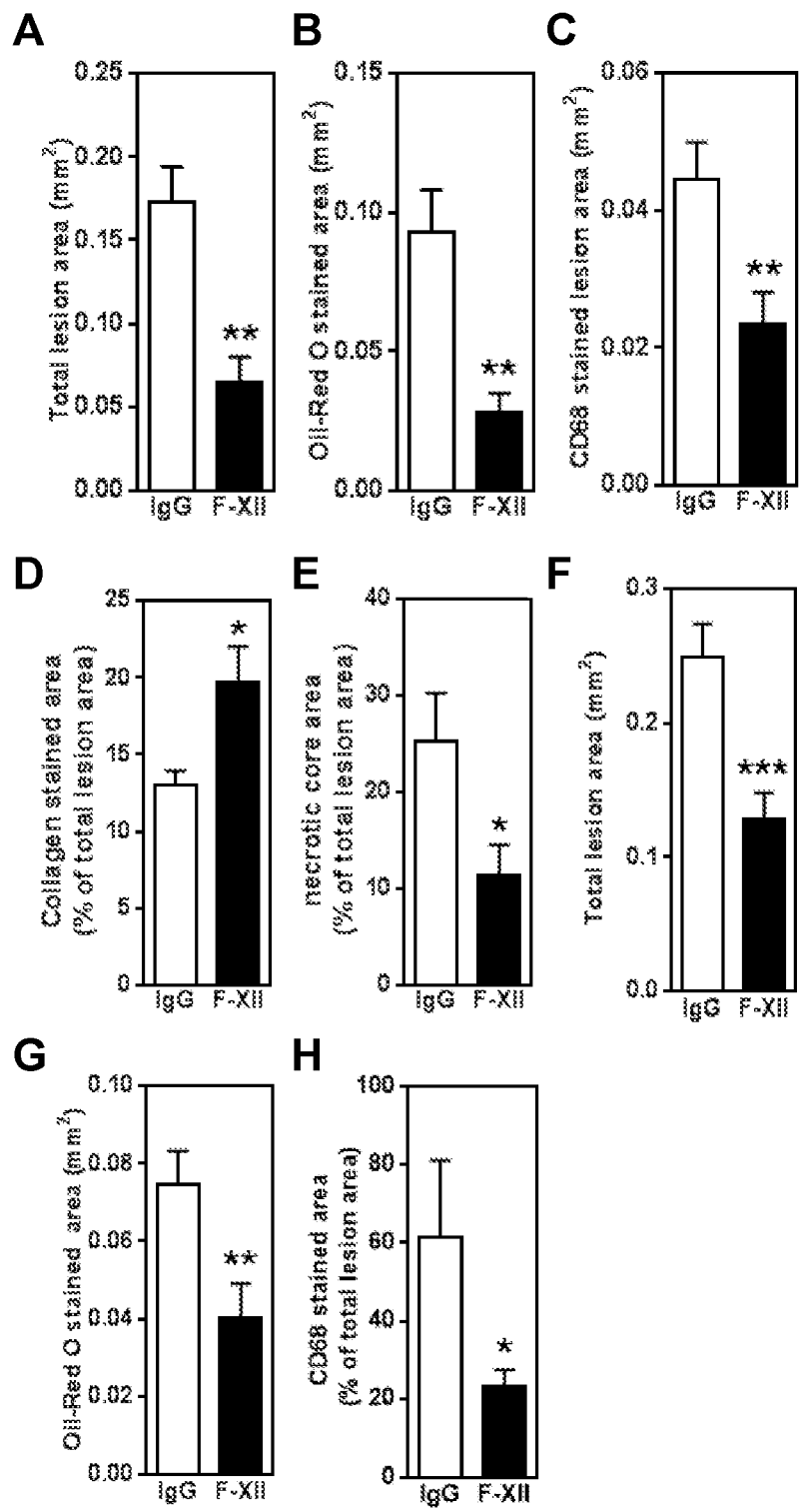
FIG. 1 is a graphical representation showing the effect of anti-FXII antibody treatment on atherosclerosis development in aortic sinus lesions (A-E) and aortic arch lesions (F-H). Anti-FXII antibody treatment attenuates total lesion size (A, F); lipid accumulation (B, G), macrophage numbers (C, H), collagen accumulation (D) and necrotic core area (E). Mean±SEM; n=6; *: $P<0.05$ compared to control, unpaired T-test.

SEQ ID NO: 1 is an amino acid sequence of wild-type Infestin-4

SEQ ID NO: 2 is an amino acid sequence of wild-type SPINK-1

SEQ ID NO: 3 is an amino acid sequence of SPINK-1 mutant K1

SEQ ID NO: 4 is an amino acid sequence of SPINK-1 mutant K2

SEQ ID NO: 5 is an amino acid sequence of SPINK-1 mutant K3

SEQ ID NO: 6 is an amino acid sequence from the $V_H$ of anti-FXII antibody 3F7

SEQ ID NO: 7 is an amino acid sequence from the $V_L$ of anti-FXII antibody 3F7

SEQ ID NO: 8 is an amino acid sequence from a $V_H$ CDR1 of an anti-FXII antibody SEQ ID NO: 9 is an amino acid sequence from a $V_H$ CDR2 of an anti-FXII antibody SEQ ID NO: 10 is an amino acid sequence from a $V_H$ CDR2 of an anti-FXII antibody SEQ ID NO: 11 is an amino acid sequence from a $V_H$ CDR3 of an anti-FXII antibody SEQ ID NO: 12 is an amino acid sequence from a $V_H$ CDR3 of an anti-FXII antibody SEQ ID NO: 13 is an amino acid sequence from a $V_L$ CDR1 of an anti-FXII antibody SEQ ID NO: 14 is an amino acid sequence from a $V_L$ CDR2 of an anti-FXII antibody SEQ ID NO: 15 is an amino acid sequence from a $V_L$ CDR3 of an anti-FXII antibody SEQ ID NO: 16 is an amino acid sequence from a $V_L$ CDR3 of an anti-FXII antibody SEQ ID NO: 17 is an amino acid sequence from a $V_L$ CDR1 of an anti-FXII antibody SEQ ID NO: 18 is an amino acid sequence of the $V_H$ of anti-FXII antibody gVR115

SEQ ID NO: 19 is an amino acid sequence of the $V_L$ of anti-FXII antibody gVR115

SEQ ID NO: 20 is an amino acid sequence of the heavy chain of anti-FXII antibody gVR115

SEQ ID NO: 21 is an amino acid sequence of the light chain of anti-FXII antibody gVR115

SEQ ID NO: 22 is an amino acid sequence from a human Factor XII

SEQ ID NO: 23 is an amino acid sequence of a mature form of human albumin

SEQ ID NO: 24 is an amino acid sequence of an Infestin-4 variant

SEQ ID NO: 25 is an amino acid sequence of an Infestin-4 variant

DESCRIPTION

General

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or groups of compositions of matter.

Those skilled in the art will appreciate that the present disclosure is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific examples described herein, which are intended for the purpose of exemplification only. Functionally-equivalent products, compositions and methods are clearly within the scope of the present disclosure.

Any example of the present disclosure herein shall be taken to apply mutatis mutandis to any other example of the disclosure unless specifically stated otherwise.

Unless specifically defined otherwise, all technical and scientific terms used herein shall be taken to have the same meaning as commonly understood by one of ordinary skill in the art (for example, in cell culture, molecular genetics, immunology, immunohistochemistry, protein chemistry, and biochemistry).

Unless otherwise indicated, the recombinant protein, cell culture, and immunological techniques utilized in the present disclosure are standard procedures, well known to those skilled in the art. Such techniques are described and explained throughout the literature in sources such as, J. Perbal, A Practical Guide to Molecular Cloning, John Wiley and Sons (1984), J. Sambrook et al. Molecular Cloning: A Laboratory Manual, Cold Spring Harbor Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbor Laboratory, (1988), and J. E. Coligan et al. (editors) Current Protocols in Immunology, John Wiley & Sons (including all updates until present).

The description and definitions of variable regions and parts thereof, immunoglobulins, antibodies and fragments thereof herein may be further clarified by the discussion in Kabat Sequences of Proteins of Immunological Interest, National Institutes of Health, Bethesda, Md., 1987 and 1991, Bork et al., J Mol. Biol. 242, 309-320, 1994, Chothia and Lesk J. Mol Biol. 196:901-917, 1987, Chothia et al. Nature 342, 877-883, 1989 and/or or Al-Lazikani et al., J Mol Biol 273, 927-948, 1997.

Any discussion of a protein or antibody herein will be understood to include any variants of the protein or antibody produced during manufacturing and/or storage. For example, during manufacturing or storage an antibody can be deamidated (e.g., at an asparagine or a glutamine residue) and/or have altered glycosylation and/or have a glutamine residue converted to pyroglutamine and/or have a N-terminal or C-terminal residue removed or "clipped" and/or have part or all of a signal sequence incompletely processed and, as a consequence, remain at the terminus of the antibody. It is understood that a composition comprising a particular amino acid sequence may be a heterogeneous mixture of the stated or encoded sequence and/or variants of that stated or encoded sequence.

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

As used herein the term "derived from" shall be taken to indicate that a specified integer may be obtained from a particular source albeit not necessarily directly from that source.

Selected Definitions

Coagulation Factor XII, also known as Hageman factor or FXII, is a plasma protein. It is the zymogen form of Factor XIIa, an enzyme of the serine protease (or serine endopeptidase) class. In humans, Factor XII is encoded by the F12 gene. For the purposes of nomenclature only and not limitation exemplary sequences of human Factor XII is set out in NCBI Reference Sequence: NP_000496.2; in NCR protein accession number NP_000496 and in SEQ ID NO: 22. Additional sequences of Factor XII can be determined using sequences provided herein and/or in publically available databases and/or determined using standard techniques (e.g., as described in Ausubel et al., (editors), Current Protocols in Molecular Biology, Greene Pub. Associates and Wiley-Interscience (1988, including all updates until present) or Sambrook et al., Molecular Cloning: A Laboratory Manual, Cold Spring Harbor Laboratory Press (1989)).

As used herein, the term "Factor XII inhibitor" or "FXII inhibitor" or "inhibitor of FXII" refers to an inhibitor of either or both of Factor XII (prior to activation, i.e., its zymogen) and activated Factor XII (FXIIa) as well as to the activation of FXII. Thus, "inhibitor(s) of FXII" can include inhibitors of either or both of FXII and FXIIa (also termed αFXIIa) as well as the activation of FXII, including the FXIIa cleavage products FXIIa alpha and FXIIa beta (also termed FXIIf). FXII inhibitors encompass functional variants and fragments of the wild-type inhibitor. A functional variant or fragment is a molecule that retains at least 50% (e.g., about 50%, or about 60%, or about 70%, or about 80%, or about 90%, or about 95%, or about 99%, or about 100%) of the ability of the wild-type molecule to inhibit FXII, FXIIa or the activation of FXII. In one example, the FXII inhibitors are non-endogenous inhibitors; that is, they are not inhibitors that occur naturally in the human or animal body.

The term "direct FXII inhibitor" or "direct inhibitor", as used herein, refers to an inhibitor that acts via contact (e.g., binding) with FXII (or FXIIa), i.e., the FXII inhibitor binds to FXII and/or FXIIa and inhibits its activity and/or activation. In contrast, an indirect inhibitor may act without contacting FXII (or FXIIa) protein. For example, antisense RNA can be used to decrease expression of the FXII gene, or a small molecule can inhibit the effects of FXIIa via interactions with downstream FXIIa reaction partners like Factor XI; these do not interact directly with the FXII protein. Thus, an indirect inhibitor, in contrast to a direct inhibitor, acts upstream or downstream from the FXII protein. In one example, the FXII inhibitors are specific to FXII or FXIIa, in particular specific to human FXII or FXIIa.

As used herein, the term "binds" in reference to the interaction of a protein or an antigen binding site thereof with an antigen means that the interaction is dependent upon the presence of a particular structure (e.g., an antigenic determinant or epitope) on the antigen. For example, an antibody recognizes and binds to a specific protein structure rather than to proteins generally. If an antibody binds to epitope "A", the presence of a molecule containing epitope "A" (or free, unlabeled "A"), in a reaction containing labeled "A" and the protein, will reduce the amount of labeled "A" bound to the antibody.

As used herein, the term "specifically binds" or "binds specifically" shall be taken to mean that a protein or an antigen binding site thereof reacts or associates more frequently, more rapidly, with greater duration and/or with greater affinity with a particular antigen or cell expressing same than it does with alternative antigens or cells. For example, a protein or an antigen binding site thereof binds to FXII (or FXIIa) with materially greater affinity (e.g., 1.5 fold or 2 fold or 5 fold or 10 fold or 20 fold or 40 fold or 60 fold or 80 fold to 100 fold or 150 fold or 200 fold) than it does to other blood clotting factors or to antigens commonly recognized by polyreactive natural antibodies (i.e., by naturally occurring antibodies known to bind a variety of antigens naturally found in humans). Generally, but not necessarily, reference to binding means specific binding, and each term shall be understood to provide explicit support for the other term.

The term "amidolytic activity" refers to the ability of the inhibitor of FXII to catalyse the hydrolysis of at least one peptide bond in another polypeptide.

The term "identity" or "identical" as used herein refers to the percentage number of amino acids that are identical or constitute conservative substitutions. Homology may be determined using sequence comparison programs such as GAP (Deveraux et al., 1984, Nucleic Acids Research 12, 387-395), which is incorporated herein by reference. In this way sequences of a similar or substantially different length to those cited herein could be compared by insertion of gaps into the alignment, such gaps being determined, for example, by the comparison algorithm used by GAP.

A "half-life enhancing polypeptide" or "HLEP" is a polypeptide fusion partner that may increase the half-life of the FXII inhibitor in vivo in a patient or in an animal. Examples include albumin and immunoglobulins and their fragments, such as Fc domains, or derivatives, which may be fused to a FXII inhibitor directly or via a cleavable or non-cleavable linker. Ballance et al. (WO 2001/79271) described fusion polypeptides comprising a multitude of different therapeutic polypeptides fused to human serum albumin.

As used herein, the terms "albumin" and "serum albumin" encompass human albumin (HA) and variants thereof. For the purposes of nomenclature only and not limitation exemplary sequences of the full mature form of albumin is set out in SEQ ID NO: 23, as well as albumin from other species and variants thereof. As used herein, "albumin" refers to an albumin polypeptide or amino acid sequence, or an albumin variant, having one or more functional activities (e.g. biological activities) of albumin. In certain examples, albumin is used to stabilize or prolong the therapeutic activity of a FXII inhibitor. The albumin may be derived from any vertebrate, especially any mammal, for example human, monkey, cow, sheep, or pig. Non-mammalian albumin can also be used and includes, but is not limited to, albumin from chicken and salmon. The albumin portion of the albumin-linked polypeptide may be from a different animal than the therapeutic polypeptide portion. See WO 2008/098720 for examples of albumin fusion proteins, incorporated herein by reference in its entirety.

The term "recombinant" shall be understood to mean the product of artificial genetic recombination. Accordingly, in the context of a recombinant protein comprising an antibody variable region, this term does not encompass an antibody naturally-occurring within a subject's body that is the product of natural recombination that occurs during B cell maturation. However, if such an antibody is isolated, it is to be considered an isolated protein comprising an antibody variable region. Similarly, if nucleic acid encoding the protein is isolated and expressed using recombinant means, the resulting protein is a recombinant protein. A recombinant protein also encompasses a protein expressed by artificial recombinant means when it is within a cell, tissue or subject, e.g., in which it is expressed.

The term "protein" shall be taken to include a single polypeptide chain, i.e., a series of contiguous amino acids linked by peptide bonds or a series of polypeptide chains covalently or non-covalently linked to one another (i.e., a polypeptide complex). For example, the series of polypeptide chains can be covalently linked using a suitable chemical or a disulfide bond. Examples of non-covalent bonds include hydrogen bonds, ionic bonds, Van der Waals forces, and hydrophobic interactions.

The term "polypeptide" or "polypeptide chain" will be understood from the foregoing paragraph to mean a series of contiguous amino acids linked by peptide bonds.

The skilled artisan will be aware that an "antibody" is generally considered to be a protein that comprises a variable region made up of a plurality of polypeptide chains, e.g., a polypeptide comprising a light chain variable region ($V_L$) and a polypeptide comprising a heavy chain variable region ($V_H$). An antibody also generally comprises constant domains, some of which can be arranged into a constant region, which includes a constant fragment or fragment crystallizable (Fc), in the case of a heavy chain. A $V_H$ and a $V_L$ interact to form a Fv comprising an antigen binding region that is capable of specifically binding to one or a few closely related antigens. Generally, a light chain from mammals is either a κ light chain or a λ light chain and a heavy chain from mammals is α, δ, ε, γ, or μ. Antibodies can be of any type (e.g., IgG, IgE, IgM, IgD, IgA, and IgY), class (e.g., $IgG_1$, $IgG_2$, $IgG_3$, $IgG_4$, $IgA_1$ and $IgA_2$) or subclass. The term "antibody" also encompasses humanized antibodies, primatized antibodies, human antibodies, synhumanized antibodies and chimeric antibodies.

An "anti-FXII antibody" includes antibodies that bind to and/or inhibit either or both of the zymogen of FXII and the activated protein (FXIIa), including the FXIIa alpha and FXIIa beta cleavage fragments. In some examples, the antibody binds specifically to FXIIa or the alpha or beta chain fragments of FXIIa.

The terms "full-length antibody," "intact antibody" or "whole antibody" are used interchangeably to refer to an antibody in its substantially intact form, as opposed to an antigen binding fragment of an antibody. Specifically, whole antibodies include those with heavy and light chains including an Fc region. The constant domains may be wild-type sequence constant domains (e.g., human wild-type sequence constant domains) or amino acid sequence variants thereof.

As used herein, "variable region" refers to the portions of the light and/or heavy chains of an antibody as defined herein that is capable of specifically binding to an antigen and includes amino acid sequences of complementarity determining regions (CDRs); i.e., CDR1, CDR2, and CDR3, and framework regions (FRs). Exemplary variable regions comprise three or four FRs (e.g., FR1, FR2, FR3 and optionally FR4) together with three CDRs. In the case of a protein derived from an IgNAR, the protein may lack a CDR2. $V_H$ refers to the variable region of the heavy chain. $V_L$ refers to the variable region of the light chain.

As used herein, the term "complementarity determining regions" (syn. CDRs; i.e., CDR1, CDR2, and CDR3) refers to the amino acid residues of an antibody variable domain the presence of which are necessary for antigen binding. Each variable domain typically has three CDR regions identified as CDR1, CDR2 and CDR3. The amino acid positions assigned to CDRs and FRs can be defined according to *Kabat Sequences of Proteins of Immunological Interest*, National Institutes of Health, Bethesda, Md., 1987 and 1991 or other numbering systems in the performance of this disclosure, e.g., the canonical numbering system of Chothia and Lesk *J. Mol Biol.* 196: 901-917, 1987; Chothia et al. Nature 342, 877-883, 1989; and/or Al-Lazikani et al., *J Mol Biol* 273: 927-948, 1997; the IMGT numbering system of Lefranc et al., *Devel. And Compar. Immunol.*, 27: 55-77, 2003; or the AHO numbering system of Honnegher and Plükthun *J. Mol. Biol.*, 309: 657-670, 2001.

"Framework regions" (FRs) are those variable domain residues other than the CDR residues. As used herein, the term "variable region fragment" or "Fv" shall be taken to mean any protein, whether comprised of multiple polypeptides or a single polypeptide, comprising a $V_L$ and a $V_H$, wherein the $V_L$ and a $V_H$ are associated to form a complex having an antigen binding site, i.e., capable of specifically binding to an antigen. The $V_H$ and the $V_L$ which form the antigen binding site can be in a single polypeptide chain or in different polypeptide chains. Furthermore, an Fv of the disclosure (as well as any protein of the disclosure) may have multiple antigen binding sites which may or may not bind the same antigen. This term shall be understood to encompass fragments directly derived from an antibody as well as proteins corresponding to such a fragment produced using recombinant means. In some examples, the $V_H$ is not linked to a heavy chain constant domain $(C_H)1$ and/or the $V_L$ is not linked to a light chain constant domain (CL). Exemplary Fv containing polypeptides or proteins include a Fab fragment, a Fab' fragment, a F(ab') fragment, a scFv, a diabody, a triabody, a tetrabody or higher order complex, or any of the foregoing linked to a constant region or domain thereof, e.g., $C_H2$ or $C_H3$ domain, e.g., a minibody or an antibody. A "Fab fragment" consists of a monovalent antigen-binding fragment of an antibody, and can be produced by digestion of a whole antibody with the enzyme papain, to yield a fragment consisting of an intact light chain and a portion of a heavy chain or can be produced using recombinant means. A "Fab' fragment" of an antibody can be obtained by treating a whole antibody with pepsin, followed by reduction, to yield a molecule consisting of an intact light chain and a portion of a heavy chain comprising a $V_H$ and a single constant domain. Two Fab' fragments are obtained per antibody treated in this manner. A Fab' fragment can also be produced by recombinant means. A "F(ab')2 fragment" of an antibody consists of a dimer of two Fab' fragments held together by two disulfide bonds, and is obtained by treating a whole antibody molecule with the enzyme pepsin, without subsequent reduction. A "Fab$_2$" fragment is a recombinant fragment comprising two Fab fragments linked using, for example a leucine zipper or a $C_H3$ domain. A "single chain Fv" or "scFv" is a recombinant molecule containing the Fv of an antibody in which the variable region of the light chain and the variable region of the heavy chain are covalently linked by a suitable, flexible polypeptide linker. As will be apparent from the foregoing discussion, this term encompasses an antibody or an antigen binding fragment thereof comprising a $V_H$ and a $V_L$.

As used herein, the terms "preventing", "prevent" or "prevention" include administering a compound of the disclosure to thereby stop or hinder the development of at least one symptom of a condition.

As used herein, the terms "treating", "treat" or "treatment" include administering a protein described herein to thereby reduce or eliminate at least one symptom of a specified disease or condition or to slow progression of the disease or condition.

As used herein, the term "subject" shall be taken to mean any animal including humans, for example a mammal. Exemplary subjects include but are not limited to humans and non-human primates. For example, the subject is a human.

Treating or Preventing Atherosclerotic Lesions

The disclosure herein provides, for example, a method for treating or preventing atherosclerosis in a subject comprising administering to the subject an inhibitor of Factor XII.

The disclosure also provides, a method for preventing atherosclerotic plaque rupture in a subject comprising administering to the subject an inhibitor of Factor XII.

In one example, the subject suffers from atherosclerosis, or atherosclerotic lesions. The atherosclerotic lesion can be stable or unstable. In one example, the atherosclerotic lesion is unstable. For example, a subject suffering from atherosclerosis has suffered a clinically acceptable symptom of atherosclerosis, such as:
  chest pain on exertion or angina;
  chest pain at rest;
  pain in the arms, shoulder, abdomen, or jaw;
  cardiac arrest;
  shortness of breath;
  being generally unwell;
  numbness or weakness in the subject's arm(s) or leg(s);
  difficulty speaking or slurred speech;
  temporary loss of vision;
  drooping muscles in the subject's face; and/or
  fatigue.

In one example, the subject has suffered or suffers from a condition associated with atherosclerosis. For example, the subject has suffered a myocardial infarct. In one example, the subject has suffered a stroke.

The methods of the present disclosure can be readily applied to any form of atherosclerosis in the arterial system. For example, the subject can present with sign(s) and/or symptoms of atherosclerosis of the heart, or brain, or legs, or pelvis, or arms, or kidneys. Thus, the methods of the present disclosure will be taken to apply to treating or preventing atherosclerosis in the arterial system.

In one example, the subject is at risk of developing atherosclerosis, or atherosclerotic lesions, but the onset of atherosclerosis has not yet occurred. A subject is at risk if he or she has a higher risk of developing atherosclerosis than a control population. The control population may include one or more subjects selected at random from the general population (e.g., matched by age, gender, race and/or ethnicity) who have not suffered from or have a family history of angina, stroke and/or heart attack. A subject can be considered at risk for atherosclerosis if a "risk factor" associated with atherosclerosis is found to be associated with that subject. A risk factor can include any activity, trait, event or property associated with a given disorder, for example, through statistical or epidemiological studies on a population of subjects. A subject can thus be classified as being at risk for atherosclerosis even if studies identifying the underlying risk factors did not include the subject specifically. For example, a subject who has high plasma low density lipoprotein levels is at risk of developing atherosclerosis because the frequency of atherosclerosis is increased in a population of subjects who have high plasma low density lipoprotein levels as compared to a population of subjects who do not.

In one example, a subject at risk of atherosclerosis include those patients who are hyper-cholesterolemic, diabetic, obese and/or hypertensive. Subjects especially at a high risk are those who have already suffered from angina, and/or stroke and/or heart attack.

As discussed above, methods of the disclosure achieve one or more of the following effects:
  reducing the likelihood of occlusive arterial thrombus in a subject;
  reducing atherosclerotic plaque lesion size in a subject;
  increasing plaque stabilization in a subject;
  reducing inflammatory cell accumulation in an atherosclerotic plaque lesion in a subject; and/or
  reducing pro-atherogenic cell populations in a subject.

Methods for assessing plaque lesion size are known in the art and include, for example, angiographic analysis, intravascular ultrasound or optical coherence tomography (OCT).

Methods for assessing plaque stabilization are known in the art and include, for example, intravascular ultrasound analysis or MRI of carotid arteries.

In one example, a method of the disclosure reduces any symptom of atherosclerosis known in the art or described herein.

As will be apparent to the skilled person a "reduction" in a symptom or effect of atherosclerosis in a subject will be comparative to another subject who has also suffered from atherosclerosis but who has not received treatment with a method described herein or to the subject prior to treatment. This does not necessarily require a side-by-side comparison of two subjects. Rather population data can be relied upon. For example a population of subjects suffering from atherosclerosis who have not received treatment with a method described herein (optionally, a population of similar subjects to the treated subject, e.g., age, weight, diabetic status, cholesterol levels) are assessed and the mean values are compared to results of a subject or population of subjects treated with a method described herein.

Inhibitors of Factor XII

In one example, the inhibitor of FXII is a direct FXII inhibitor, such as a specific FXII inhibitor. For example, the specific FXII inhibitor inhibits plasmatic serine proteases or other endogenous proteins other than FXII and/or FXIIa less than or equal to about 25% if used in a molar ratio of 1:1. For example, the specific inhibitor of FXII/FXIIa inhibitor inhibits plasmatic serine proteases other than FXII and/or FXIIa less than or equal to about 25% when said inhibitor is used in a molar ratio of 1:1 of the respective plasmatic serine protease to said inhibitor. In one example, the FXII inhibitor inhibits plasmatic serine proteases other than FXII and/or FXIIa less than or equal to about 20%, or less than or equal to about 15%, or less than or equal to about 10%, or less than or equal to about 5%, or less than or equal to about 1% if used in a molar ratio of 1:1. For example, a specific FXII antibody inhibits the plasmatic serine protease FXIa by about 5%, wherein the molar ratio of FXIa to said antibody is 1:1 whereas the same FXII antibody inhibits FXIIa by at least about 80%, or at least about 90%.

In one example, one other plasmatic serine protease is inhibited by more than about 50% if used in a molar ratio of 1:1 of the respective plasmatic serine protease to the inhibitor.

In another example of the disclosure, two other plasmatic serine proteases are inhibited by more than about 50% if used in a molar ratio of 1:1 of the respective plasmatic serine protease to the inhibitor.

Serine Protease Inhibitors

In one example, the inhibitor of FXII is a serine protease inhibitor. For example, the inhibitor of FXII comprises a sequence corresponding to Infestin-4 or variants thereof. In one example, the inhibitor of FXII comprises a sequence corresponding to SPINK-1 or variants thereof.

Infestin-4

In one example, the disclosure provides an inhibitor of FXII comprising infestin domain 4 (referred to as "Infestin-4"). Infestins are a class of serine protease inhibitors derived from the midgut of the hematophagous insect, *Triatoma infestans*, a major vector for the parasite *Trypanosoma cruzi*, known to cause Chagas disease. (Campos I T N et al. 32 Insect Biochem. Mol. Bio. 991-997, 2002; Campos I T N et al. 577 FEBS Lett. 512-516, 2004; WO 2008/098720.) This insect uses these inhibitors to prevent coagulation of ingested blood. The infestin gene encodes 4 domains that result in proteins that can inhibit different factors in the coagulation pathway. In particular, domain 4 encodes a protein (Infestin-4) that is a strong inhibitor of FXIIa. Infestin-4 has been administered in mice without resulting in bleeding complications. (WO 2008/098720; Hagedorn et al., Circulation 2010; 121:1510-17.)

In one embodiment, the inhibitor of FXII comprises Infestin-4. The term "Infestin-4," as used herein, encompasses variants or fragments of the wild-type peptide that retain the ability to inhibit FXII. For the purposes of nomenclature only and not limitation an exemplary sequence of Infestin-4 is set out in SEQ ID NO: 1.

In one example, the Infestin-4 is chosen for its ability to inhibit FXIIa. In one example, the Infestin-4 comprises a variant of Infestin-4, wherein the variant comprises Infestin domain 4, and optionally, Infestin domains 1, 2, and/or 3. In one example, the Infestin-4 is a $(His)_6$-tagged Infestin-4 construct.

In another example, the Infestin-4 is a fusion protein comprising a fusion partner, such as a half-life enhancing polypeptide (e.g., albumin, an Fc domain of an IgG, or PEG), linked or bound to infestin-4. In one example, a linker connects the fusion partner to Infestin-4. In various embodiments, the Infestin-4 is the rHA-Infestin-4 protein described in Hagedorn et al., Circulation 2010; 117:1153-60. In one example, a composition comprises albumin bound to the rHA-Infestin-4 protein described in Hagedorn et al., Circulation 2010; 117:1153-60, by a flexible linker. In another example, other Infestin-4 inhibitors of FXII are used, examples of which are described in WO 2008/098720 and Hagedorn et al., Circulation 2010; 117:1153-60, both of which are incorporated by reference in their entirety.

In one example, the inhibitor of FXII is a variant of Infestin-4. As used here, the term "variant" of Infestin-4 refers to a polypeptide with one or more amino acid mutation, wherein "mutation" is defined as a substitution, a deletion, or an addition, to the wild type Infestin-4 sequence (SEQ ID NO: 1). The term "variant" of Infestin-4 also includes functional fragments of the wild type or a mutated Infestin-4 sequence.

In one example, the one or more mutations to the wild type Infestin-4 sequence do not substantially alter the functional ability of the polypeptide to inhibit FXII. For example, the one or more mutations do not completely or substantially remove the ability of the polypeptide to inhibit FXII. For example, the variant retains at least about 20%, or about 30%, or about 40%, or about 50%, or about 60%, or about 70%, or about 80%, or about 90%, or about 95%, or about 98%, or about 99%, or more of the inhibitory ability of wild type Infestin-4.

In one example, the inhibitor of FXII comprises an Infestin-4 variant comprising residues 2-13 from the amino terminal of the wild type Infestin-4 sequence as set forth in SEQ ID NO: 1. For example, the Infestin-4 variant comprises the amino acid sequence set forth in SEQ ID NO: 24.

In one example, the inhibitor of FXII comprises an Infestin-4 variant comprising residues 2-13 of SEQ ID NO: 1 and also comprising at least one amino acid mutations, as compared to the wild type Infestin-4 sequence (SEQ ID NO: 1), outside residues 2-13 of SEQ ID NO: 1. For example, the Infestin-4 variant comprises at least two amino acid mutations, or at least three amino acid mutations, or at least four amino acid mutations, or at least five amino acid mutations. For example, the inhibitor of FXII comprises a polypeptide sequence comprising SEQ ID NO: 1 modified to contain between 1 and 5 amino acid mutations outside of N-terminal amino acid positions 2-13 of SEQ ID NO: 1.

In one example, the inhibitor of FXII is an Infestin-4 variant which retains six conserved cysteine residues from the wild type Infestin-4 sequence. In one example, the six conserved cysteine residues are amino acids at positions 6, 8, 16, 27, 31, and 48 of the wild type Infestin-4 sequence (SEQ ID NO: 1). In one example, the Infestin-4 variant comprises the final conserved cysteine at position 48. In another example, the exact positions of the cysteine residues, and relative positions to each other, may change from positions 6, 8, 16, 27, 31, and 48 of the wild type Infestin-4 sequence due to insertions or deletions in the Infestin-4 variant sequence.

In one example, the Infestin-4 variant is at least about 70% identical to the wild type Infestin-4 sequence. For example, the Infestin-4 has an identity of at least about 75%, at least about 80%, at least about 85%, at least about 90%, at least about 95%, at least about 98%, or at least about 99% to the wild type Infestin-4 sequence. For example, the inhibitor of FXII comprises a polypeptide sequence comprising a sequence at least 70% identical to SEQ ID NO: 1 and retaining six conserved cysteine residues from SEQ ID NO: 1.

In one example, the inhibitor of FXII is an Infestin-4 variant retains six conserved cysteine residues from the wild type Infestin-4 sequence and/or has a sequence of at least about 70% identical to the wild type Infestin-4 sequence.

In one example, the inhibitor of FXII is an Infestin-4 variant comprising SEQ ID NO: 1 modified to contain 1-5 amino acid mutations outside of N-terminal amino acid positions 2-13 of SEQ ID NO: 1; and a sequence at least 70% identical to SEQ ID NO: 1 and retaining six conserved cysteine residues from SEQ ID NO: 1.

In one example, an Infestin-4 variant comprises the conserved N-terminal region amino acids 2-13 of the wild type Infestin-4 sequence, and at least one, and optionally up to five, amino acid mutations outside these conserved N-terminal amino acids, resulting in differences from the wild type Infestin-4 sequence. As used here, the term "outside the N-terminal amino acids" of an Infestin variant refers to any amino acid along the polypeptide chain of the variant other than the contiguous stretch of amino acids that comprises the sequence of SEQ ID NO: 24, which are amino acids 2-13 from SEQ ID NO: 1.

In one example, an Infestin-4 variant comprises all six conserved cysteine residues from SEQ ID NO: 1 and/or a sequence at least about 70% identical to the wild type Infestin-4 sequence (SEQ ID NO: 1). For example, the Infestin-4 variant may comprise a sequence with about 70%, or about 75%, or about 85%, or about 90%, or about 91%, or about 92%, or about 93%, or about 94%, or about 95%, or about 96%, or about 97%, or about 98% or about 99% identity to the wild type Infestin-4 sequence (SEQ ID NO: 1).

In one example, the Infestin-4 variant retains amino acids 2-13 from SEQ ID NO: 1 as well as all six conserved cysteine residues, and is at least about 70% identical to the wild type Infestin-4 sequence (SEQ ID NO: 1). For example, the Infestin-4 variant may comprise a sequence with about 70%, or about 75%, or about 85%, or about 90%, or about 91%, or about 92%, or about 93%, or about 94%, or about 95%, or about 96%, or about 97%, or about 98% or about 99% identity to the wild type Infestin-4 sequence (SEQ ID NO: 1).

In one embodiment, the FXII inhibitor comprises variant of the wild type Infestin-4 polypeptide sequence, wherein the Infestin-4 variant comprises the N-terminal amino acids 2-13 of SEQ ID NO: 1; at least one, and optionally up to five, amino acid mutations outside the N-terminal amino acids; six conserved cysteine residues; and/or at least 70% identity to the wild type Infestin-4 sequence (SEQ ID NO: 1). For example, the Infestin-4 variant comprises a sequence with at least 75%, at least 80%, at least 85%, at least 90%, at least 95%, at least 98%, or at least 99% identity to the wild type Infestin-4 sequence (SEQ ID NO: 1).

In one example, an Infestin-4 variant comprises the sequence set forth in SEQ ID NO: 25. In one example, SEQ ID NO: 24 is added at or near the N-terminus of a fragment or full length wild type Infestin-4 sequence (SEQ ID NO: 1) and derives from the human protein SPINK-1.

In one example, an Infestin-4 comprises a fusion construct between wild-type Infestin-4 or a variant Infestin-4 and a fusion partner. For example, the fusion partner comprises a PEG or half-life enhancing polypeptide. In one example, the Infestin the half-life enhancing polypeptide comprises human albumin (referred to as "HA"). In some embodiments, the HA is a recombinant protein (referred to as "rHA"). In certain embodiments, the Infestin-4 and HA proteins are joined directly, or via a linker peptide. For example, the inhibitor of FXII is a fusion protein comprising human albumin linked to an Infestin-4 via a linker peptide.

In one example, the inhibitor of FXII is a variant of Infestin-4 that retains the ability to inhibit FXII. For example, the variant of Infestin-4 has the same ability as Infestin-4 to inhibit FXII. In one example, the variant of Infestin-4 inhibits FXII activity and/or activation of FXII.

In one example, the inhibitor of FXII of the present disclosure competes with Infestin-4 for binding to human Factor XIIa-beta.

Methods for assessing functional inhibitory activity of FXII are known in the art and include, for example, in vitro and/or in vivo characterization, including direct assays to test inhibition of FXII enzyme activity, prolonged coagulation time (e.g., activated partial thromboplastin time, aPTT), clinical clotting tests that address the intrinsic pathway of coagulation, or in vivo methods that evaluate coagulation.

SPINK-1

In one example, the inhibitor of FXII comprises a human protein with high similarity to Infestin-4. For example, the inhibitor of FXII is SPINK-1. SPINK-1 is a Kazal-type serine protease inhibitor expressed in the pancreas (also known as pancreatic secretory trypsin inhibitor, or PSTI). The Kazal-type serine protease inhibitor family is one of numerous families of known serine protease inhibitors. Many similar proteins from different species have been described (Laskowski M and Kato I, 49 Ann. Rev. Biochem. 593-626, 1980.). For the purposes of nomenclature only and not limitation an exemplary sequence of SPINK-1 is set out in SEQ ID NO: 2.

In one example, the inhibitor of FXII comprises the wild-type sequence of SPINK-2 as set out in SEQ ID NO: 2.

The term "SPINK-1" also encompasses functional variants and fragments of SPINK-1 that substantially retain the ability to inhibit FXII. In one example, the inhibitor of FXII is a SPINK-1 variant. For example, variants of the wild-type sequence (i.e., SEQ ID NO: 2) may be generated in order to increase the identity of the SPINK-1 sequence to Infestin-4. As used herein, the term "variant" includes fragments of a SPINK-1 or mutated SPINK-1 sequence.

In one example, SPINK-1 (SEQ ID NO: 2) is mutated to replace the N-terminal amino acids at positions 2-13 with the N-terminal amino acids 2-13 of SEQ ID NO: 1.

In one example, the inhibitor of FXII is a SPINK-1 variant comprising an N-terminal portion of a wild type Infestin-4 sequence. For example, the SPINK-1 variant comprises amino acids 2-13 of SEQ ID NO: 1.

In one example, the inhibitor of FXII is a SPINK-1 variant comprising at least one additional amino acid mutation outside the N-terminal amino acids that increase the identity of the SPINK-1 variant to the wild type Infestin-4 sequence. For example, the SPINK-1 variant comprises at least one, or at least two, or at least three, or at least four, or at least five additional amino acid mutations outside the N-terminal amino acids that increase the identity of the SPINK-1 variant to the wild type Infestin-4 sequence.

A mutation may comprise a substitution, a deletion, and/or an addition. A mutation that is "outside the N-terminal amino acids" refers to one or more mutations in any amino acids along the polypeptide chain of the variant other than the contiguous stretch of amino acids that comprises the sequence SEQ ID NO: 24, i.e., amino acids 2-13 of SEQ ID NO: 1.

In one example, the inhibitor of FXII comprises a polypeptide sequence comprising SEQ ID NO: 2 mutated to replace the N-terminal amino acids at positions 2-13 with the N-terminal amino acids at positions 2-13 of SEQ ID NO: 1; and optionally further modified to contain 1-5 additional amino acid mutations that increase the identity of the polypeptide sequence to sequence of SEQ ID NO: 1.

In one example, the inhibitor of FXII comprises a SPINK-1 variant comprising a SPINK-1 sequence that has been mutated to increase the identity of the variant to the wild type Infestin-4 sequence (i.e., SEQ ID NO: 1).

In one example, the SPINK-1 variant comprises an N-terminal portion of a wild type Infestin-4 sequence. For example, the SPINK-1 variant comprises the amino acids 2-13 of SEQ ID NO: 1.

In one example, the inhibitor of FXII comprises a SPINK-1 variant comprising six conserved cysteine residues of SEQ ID NO: 2.

In one example, the six conserved cysteine residues of SPINK-1 may be the amino acids at positions 9, 16, 24, 35, 38, and 56 of the wild type SPINK-1 sequence (e.g., SEQ ID NO: 2). In one example, the variant comprises the final cysteine of the wild type SPINK-1 sequence (i.e., the cysteine at position 56 of SEQ ID NO: 2). In one example, the six conserved cysteine residues are not mutated but the exact positions of the cysteine residues, and relative positions to each other, may change from positions 9, 16, 24, 35, 38, and 56 of the wild type SPINK-1 sequence due to insertions and/or deletions elsewhere in the SPINK-1 variant sequence. Nevertheless, in these examples, a SPINK-1 variant comprises all six cysteine residues.

In one example, the inhibitor of FXII comprises a SPINK-1 variant comprising a sequence at least 70% identical to SEQ ID NO: 2. For example, the SPINK-1 variant comprises a sequence at least about 75%, or at least about 80%, or at least about 85%, or at least about 90%, or at least about 95%, or at least about 98%, or at least about 99% identical to SEQ ID NO: 2.

In one example, the inhibitor of FXII comprises a SPINK-1 variant comprising a sequence at least 70% identical to SEQ ID NO: 2 and retaining six conserved cysteine residues from SEQ ID NO: 2.

In one example, the six conserved cysteine residues of SPINK-1 are not mutated. In one example, the SPINK-1 sequence is mutated to comprise an N-terminal portion of a wild type Infestin-4 sequence. For example, the SPINK-1 sequence is mutated to comprise amino acids 2-13 of SEQ ID NO: 1.

In one example, the SPINK-1 sequence is mutated to comprise an N-terminal portion of a wild type Infestin-4 sequence and/or to have a sequence at least 70% identical to the wild type SPINK-1 sequence. For example, the SPINK-1 sequence is mutated to comprise a sequence at least about 70%, or at least about 75%, or at least about 80%, or at least about 85%, or at least about 90%, or at least about 95%, or at least about 98%, or at least 99% identical to the wild type SPINK-1 sequence.

In one example, the SPINK-1 sequence is mutated to comprise an N-terminal portion of a wild type Infestin-4 sequence and/or to have a sequence at least 70% identical to the wild type SPINK-1 sequence and/or to include at least one mutation in the SPINK-1 sequence outside the N-terminal amino acids.

In one example, the inhibitor of FXII comprises a SPINK-1 variant comprising SEQ ID NO: 2 mutated to replace the N-terminal amino acids at positions 2-13 with the N-terminal amino acids at positions 2-13 of SEQ ID NO: 1; and optionally further modified to contain 1-5 additional amino acid mutations that increase the identity of the polypeptide sequence to sequence of SEQ ID NO: 1.

In one example, the inhibitor of FXII comprises a SPINK-1 variant comprising SEQ ID NO: 2 mutated to replace the N-terminal amino acids at positions 2-13 with the N-terminal amino acids at positions 2-13 of SEQ ID NO: 1; and optionally further modified to contain 1-5 additional amino acid mutations that increase the identity of the polypeptide sequence to sequence of SEQ ID NO: 1 and a sequence at least 70% identical to SEQ ID NO: 2 and retaining six conserved cysteine residues from SEQ ID NO: 2.

In one example, the inhibitor of FXII comprises a SPINK-1 variant that substantially retains its ability to inhibit FXII. For example, the SPINK-1 variant retains at least about 20%, or about 30%, or about 40%, or about 50%, or about 60%, or about 70%, or about 80%, or about 90%, or about 95%, or about 98%, or about 99% of the inhibitory activity of wild type SPINK-1.

In one example, the inhibitor of FXII of the present disclosure competes with SPINK-1 for binding to human Factor XIIa-beta.

In one example, the inhibitor of FXII is a SPINK-1 variant selected from the group consisting of K1 (SEQ ID NO: 3), K2 (SEQ ID NO: 4), and K3 (SEQ ID NO: 5).

In one example, the SPINK-1 variant is K1, as set forth in SEQ ID NO: 3.

In one example, the SPINK-1 variant is K2, as set forth in SEQ ID NO: 4.

In one example, the SPINK-1 variant is K3, as set forth in SEQ ID NO: 5.

In one example, further amino acid substitutions can be made outside of the N-terminus relative to K1 in order to increase identity to Infestin-4.

In one example, further amino acid substitutions can be made outside of the N-terminus relative to K3 in order to increase identity to Infestin-4. For example, five amino acid substitutions outside of the N-terminus relative to K3 increase identity to Infestin-4.

In one example, a SPINK-1 variant shares at least about 70% identity with the wild type SPINK-1 sequence. For example, the SPINK-1 variant shares at least about 75%, or at least about 80%, at least about 85%, or at least about 90%, or at least about 91%, or at least about 92%, or at least about 93%, or at least about 94%, or at least about 95%, or at least about 96%, or at least about 97%, or at least about 98% or at least about 99% identity with the wild type SPINK-1 sequence.

Factor XII Antibodies

An exemplary inhibitor of Factor XII (FXII) comprises an antigen variable region, e.g., is an antibody or an antigen binding fragment thereof that binds to FXII and neutralizes FXII signalling. For example, the anti-FXII antibody or antigen binding fragment thereof binds to and inhibits activation of and/or activity of FXII and/or FXIIa.

In one example, the antibody variable region specifically binds to FXII.

For example, the inhibitor of FXII binds to FXII and/or FXIIa and inhibits the activity of FXII and/or FXIIa.

In another example, the inhibitor of FXII binds to FXII and/or FXIIa and inhibits the activation of FXII to FXIIa.

Suitable antibodies and proteins comprising variable regions thereof are known in the art.

For example, anti-Factor XII antibodies and fragments thereof are described in WO 2006/066878, and in Rayon et al., Blood 86: 4134-43 (1995). Additional anti-Factor XII antibodies are described in WO 2013/014092.

In one example, the anti-FXII antibody or antigen binding fragment thereof is an antibody that binds to FXII and/or FXIIa.

In one example, the activity of FXII and/or FXIIa is inhibited by at least about 50%. For example, the activity of FXII and/or FXIIa is inhibited by about 60%, or about 70%, or about 80%, or about 85%, or about 90%, or about 95%, or about 99%, or about 100%.

In one example, the inhibitor of FXII of the present disclosure inhibits FXIIa by at least about 80%. For example, the inhibitor of FXII of the present disclosure inhibits Factor XIIa-alpha by at least about 80% when used at a molar ratio of 1:0.5 of FXIIa to inhibitor. For example, the inhibitor of FXII inhibits Factor XIIa by at least about 85%, or at least about 90%, or at least about 95%, or at least about 96%, or at least about 97%, or at least about 98%, or at least about 99%, or about 100% when used at a molar ratio of 1:0.5 of Factor XIIa to inhibitor.

Methods for detecting inhibition of Factor XIIa activity are known in the art and include, for example, an in vitro FXIIa amidolytic activity assay as disclosed in WO 2013/014092).

In one example, the anti-FXII antibody is capable of inhibiting the amidolytic activity of human Factor XIIa.

In one example, the inhibitor of FXII of the present disclosure has a binding affinity or specificity for human FXIIa that is similar to the binding affinity or specificity of antibody 3F7 or gVR115.

In one example, the inhibitor of FXII of the present disclosure competitively inhibits the binding of antibody 3F7 to FXII or gVR115.

In one example, the anti-FXII antibody has a binding affinity to human Factor XIIa-beta at least 2 fold higher than to inactivated human FXII. For example, the binding affinity to human Factor XIIa-beta is at least about 3 fold, or at least about 4 fold, or at least about 5 fold higher than to inactivated human FXII.

In one example, the inhibitor of FXII of the present disclosure binds human Factor XIIa-beta with an equilibrium dissociation constant ($K_D$) of about $1\times10^{-8}$ M or less, such as $9.5\times10^{-9}$ M or less, such as $9\times10^{-9}$ M or less, such as $8.5\times10^{-9}$ M or less, such as $8\times10^{-9}$ M or less, such as $7.5\times10^{-9}$ M or less, such as $7\times10^{-9}$ M or less, such as $6.5\times10^{-9}$ M or less, such as $6\times10^{-9}$ M or less, such as $5.5\times10^{-9}$ M or less, such as $5\times10^{-9}$ M.

In one example, the anti-FXII antibody or fragment thereof comprises a $V_H$ comprising a sequence set forth in SEQ ID NO: 6 and a $V_L$ comprising a sequence set forth in SEQ ID NO: 7.

In one example, the anti-FXII antibody or fragment thereof comprises a $V_H$ comprising a sequence which is at least 85% identical to the sequence set forth in SEQ ID NO: 6. For example, the $V_H$ sequence is at least about 90%, or at least about 95%, or at least about 98%, or at least about 99% identical to the sequence set forth in SEQ ID NO: 6. Exemplary positions for mutations to CDRs are described herein. The skilled person will be readily capable of identifying positions for mutations to framework regions. In one example, the position of any change relative to the recited sequence is in a framework region.

In one example, the anti-FXII antibody or fragment thereof comprises a $V_L$ comprising a sequence which is at least 85% identical to the sequence set forth in SEQ ID NO: 7. For example, the $V_L$ sequence is at least about 90%, or at least about 95%, or at least about 98%, or at least about 99% identical to the sequence set forth in SEQ ID NO: 7. Exemplary positions for mutations to CDRs are described herein. The skilled person will be readily capable of identifying positions for mutations to framework regions. In one example, the position of any change relative to the recited sequence is in a framework region.

In one example, the inhibitor of FXII is a protein comprising the complementary determining regions (CDRs) of the $V_H$ (SEQ ID NO: 6) and the $V_L$ (SEQ ID NO: 7) of the anti-FXII antibody. For example, the protein comprises:

(i) a $V_H$ comprising:
  (a) a sequence set forth in SEQ ID NO: 6; or
  (b) a CDR1 comprising a sequence set forth in SEQ ID NO: 8;
  (c) a CDR2 comprising a sequence set forth in SEQ ID NO: 9 or SEQ ID NO: 10;
  (d) a CDR3 comprising a sequence set forth in SEQ ID NO: 11 or SEQ ID NO: 12; and/or (ii) a $V_L$ comprising:
  (a) a sequence set forth in SEQ ID NO: 7; or
  (b) a CDR1 comprising a sequence set forth in SEQ ID NO: 13 or SEQ ID NO: 17;
  (c) a CDR2 comprising a sequence set forth in SEQ ID NO: 14;
  (d) a CDR3 comprising a sequence set forth in SEQ ID NO: 15 or SEQ ID NO: 16.

In another example, the protein comprises:

(i) a $V_H$ comprising:
  (a) a CDR1 comprising a sequence set forth in SEQ ID NO: 8;
  (b) a CDR2 comprising a sequence set forth in SEQ ID NO: 10; and
  (c) a CDR3 comprising a sequence set forth in SEQ ID NO: 12; and/or (ii) a $V_L$ comprising:
  (a) a CDR1 comprising a sequence as set forth in SEQ ID NO: 13;
  (b) a CDR2 comprising a sequence as set forth in SEQ ID NO: 14; and
  (c) a CDR3 comprising a sequence as set forth in SEQ ID NO: 16.

In one example, the protein comprises:
(i) a $V_H$ comprising:
   (a) a CDR1 comprising a sequence set forth in SEQ ID NO: 8;
   (b) a CDR2 comprising a sequence set forth in SEQ ID NO: 9; and
   (c) a CDR3 comprising a sequence set forth in SEQ ID NO: 11; and/or
(ii) a $V_L$ comprising:
   (a) a CDR1 comprising a sequence as set forth in SEQ ID NO: 13;
   (b) a CDR2 comprising a sequence as set forth in SEQ ID NO: 14; and
   (c) a CDR3 comprising a sequence as set forth in SEQ ID NO: 15.

In another example, the protein comprises:
(i) a $V_H$ comprising:
   (a) a CDR1 comprising a sequence set forth in SEQ ID NO: 8;
   (b) a CDR2 comprising a sequence set forth in SEQ ID NO: 10; and
   (c) a CDR3 comprising a sequence set forth in SEQ ID NO: 11; and/or
(ii) a $V_L$ comprising:
   (a) a CDR1 comprising a sequence as set forth in SEQ ID NO: 13;
   (b) a CDR2 comprising a sequence as set forth in SEQ ID NO: 14; and
   (c) a CDR3 comprising a sequence as set forth in SEQ ID NO: 15.

In another example, the protein comprises:
(i) a $V_H$ comprising:
   (a) a CDR1 comprising a sequence set forth in SEQ ID NO: 8;
   (b) a CDR2 comprising a sequence set forth in SEQ ID NO: 9; and
   (c) a CDR3 comprising a sequence set forth in SEQ ID NO: 11; and/or
(ii) a $V_L$ comprising:
   (a) a CDR1 comprising a sequence as set forth in SEQ ID NO: 17;
   (b) a CDR2 comprising a sequence as set forth in SEQ ID NO: 14; and
   (c) a CDR3 comprising a sequence as set forth in SEQ ID NO: 15.

In one example, the protein comprises a $V_H$ comprising a CDR1 as set forth in SEQ ID NO: 8.

In one example, the protein comprises a $V_H$ comprising a CDR1 at least 80% identical to the sequence set forth in SEQ ID NO: 8. For example, the protein comprises a $V_H$ comprising a CDR1 at least about 85%, or at least about 90%, or at least about 95%, or at least about 98%, or at least about 99% identical to the sequence set forth in SEQ ID NO: 8.

In one example, the protein comprises a $V_H$ comprising a CDR2 as set forth in SEQ ID NO: 9.

In one example, the protein comprises a $V_H$ comprising a CDR2 at least 60% identical to the sequence set forth in SEQ ID NO: 9. For example, the protein comprises a $V_H$ comprising a CDR2 at least about 70%, or at least about 80%, or at least about 85%, or at least about 90%, or at least about 95%, or at least about 98%, or at least about 99% identical to the sequence set forth in SEQ ID NO: 9.

In one example, the protein comprises a $V_H$ comprising a CDR2 as set forth in SEQ ID NO: 10.

In one example, the amino acid sequence of $V_H$ CDR2 comprises Arginine (R), Asparagine (N) or Aspartic Acid (D) at position 3 and/or Proline (P), Valine (V), Isoleucine (I) or Methionine (M) at position 4 and/or Serine (S), Proline (P) or Alanine (A) at position 5 and/or Glycine (G), Leucine (L), Valine (V) or Threonine (T) at position 6 and/or any amino acid at position 7 and/or Threonine (T), Glycine (G) or Serine (S) at position 8.

In one example, the amino acid sequence of $V_H$ CDR2 comprises Asparagine (N) at position 3 and Valine (V) at position 4 and Proline (P) at position 5 and Leucine (L) at position 6 and Tyrosine (Y) at position 7 and Glycine (G) at position 8.

In one example, the amino acid sequence of $V_H$ CDR2 comprises Asparagine (N) at position 3 and Valine (V) at position 4 and Proline (P) at position 5 and Valine (V) at position 6 and Glutamine (Q) at position 7 and Glycine (G) at position 8.

In one example, the amino acid sequence of $V_H$ CDR2 comprises Aspartic acid (D) at position 3 and Isoleucine (I) at position 4 and Proline (P) at position 5 and Threonine (T) at position 6 and Lysine (K) at position 7 and Glycine (G) at position 8.

In one example, the amino acid sequence of $V_H$ CDR2 comprises Aspartic acid (D) at position 3 and Methionine (M) at position 4 and Proline (P) at position 5 and Threonine (T) at position 6 and Lysine (K) at position 7 and Glycine (G) at position 8.

In one example, the protein comprises a $V_H$ comprising a CDR3 as set forth in SEQ ID NO: 11.

In one example, the protein comprises a $V_H$ comprising a CDR3 at least 80% identical to the sequence set forth in SEQ ID NO: 11. For example, the protein comprises a $V_H$ comprising a CDR3 at least about 85%, or at least about 90%, or at least about 95%, or at least about 98%, or at least about 99% identical to the sequence set forth in SEQ ID NO: 11.

In one example, the protein comprises a $V_H$ comprising a CDR3 as set forth in SEQ ID NO: 12.

In one example, the amino acid sequence of $V_H$ CDR3 comprises Isoleucine (I), Methionine (M) or Valine (V) at position 9 and/or Serine (S) or Lysine (K) at position 10 and/or Proline (P), Lysine (K), Threonine (T) or Histidine (H) at position 11 and/or Histidine (H), Asparagine (N), Glycine (G) or Glutamine (Q) at position 12.

In one example, the protein comprises a $V_L$ comprising a CDR1 as set forth in SEQ ID NO: 13.

In one example, the protein comprises a $V_L$ comprising a CDR1 at least 50% identical to the sequence set forth in SEQ ID NO: 13. For example, the protein comprises a $V_L$ comprising a CDR1 at least about 60%, or at least about 70%, or at least about 80%, or at least about 85%, or at least about 90%, or at least about 95%, or at least about 98%, or at least about 99% identical to the sequence set forth in SEQ ID NO: 13.

In one example, the protein comprises a $V_L$ comprising a CDR1 as set forth in SEQ ID NO: 17.

In one example, the protein comprises a $V_L$ comprising a CDR1 at least 50% identical to the sequence set forth in SEQ ID NO: 17. For example, the protein comprises a $V_L$ comprising a CDR1 at least about 60%, or at least about 70%, or at least about 80%, or at least about 85%, or at least about 90%, or at least about 95%, or at least about 98%, or at least about 99% identical to the sequence set forth in SEQ ID NO: 17.

In one example, the protein comprises a $V_L$ comprising a CDR2 as set forth in SEQ ID NO: 14.

In one example, the protein comprises a $V_L$ comprising a CDR2 at least 50% identical to the sequence set forth in SEQ ID NO: 14. For example, the protein comprises a $V_L$ comprising a CDR2 at least about 60%, or at least about 70%, or at least about 80%, or at least about 85%, or at least about 90%, or at least about 95%, or at least about 98%, or at least about 99% identical to the sequence set forth in SEQ ID NO: 14.

In one example, the protein comprises a $V_L$ comprising a CDR3 as set forth in SEQ ID NO: 15.

In one example, the protein comprises a $V_L$ comprising a CDR3 at least 50% identical to the sequence set forth in SEQ ID NO: 15. For example, the protein comprises a $V_L$ comprising a CDR3 at least about 60%, or at least about 70%, or at least about 80%, or at least about 85%, or at least about 90%, or at least about 95%, or at least about 98%, or at least about 99% identical to the sequence set forth in SEQ ID NO: 15.

In one example, the protein comprises a $V_L$ comprising a CDR3 as set forth in SEQ ID NO: 16.

In one example, the amino acid sequence of $V_L$ CDR3 comprises Alanine (A) or Serine (S) at position 2, and/or Aspartic acid (D), Tyrosine (Y), Glutamic acid (E), Threonine (T), Tryptophan (W) or Serine (S) at position 4 and/or Alanine (A), Asparagine (N), Isoleucine (I), Leucine (L), Valine (V), Proline (P), Glutamine (Q) or Glutamic acid (E) at position 5 and/or Serine (S), Aspartic acid (D), Proline (P), Glutamic acid (E), Glutamine (Q) or Arginine (R) at position 6 and/or Leucine (L) or Valine (V) at position 7 and/or Glycine (G), Leucine (L) or Lysine (K) at position 9 and/or Valine (V), Alanine (A), Aspartic acid (D), Threonine (T), Methionine (M) or Glycine (G) at position 10.

In one example, the inhibitor of FXII is an affinity matured, chimeric, CDR grafted, or humanized antibody, or antigen binding fragment thereof. In one example, the anti-FXII antibody is an affinity matured form of antibody 3F7. For example, the anti-FXII antibody is selected from VR115, VR112, VR24, VR110 or VR119 (SEQ ID NOs for HCDR 1-3 and LCDR1-3 of these antibodies are shown below in Table 1).

TABLE 1

| mAb | HCDR1 | HCDR2 | HCDR3 | LCDR1 | LCDR2 | LCDR3 |
|---|---|---|---|---|---|---|
| 3F7 | 8 | 9 | 11 | 13 | 14 | 15 |
| VR119 | 8 | 10 | 11 | 13 | 14 | 15 |
| VR112 | 8 | 10 | 11 | 13 | 14 | 15 |
| VR115 | 8 | 10 | 11 | 13 | 14 | 15 |
| VR24 | 8 | 9 | 11 | 17 | 14 | 15 |
| VR110 | 8 | 10 | 11 | 13 | 14 | 15 |

SEQ ID NO: 10 is a consensus sequence. VR119 comprises SEQ ID NO: 10 wherein the X at position 3 is N, the X at position 4 is V, the X at position 5 is P; the X at position 6 is L, the X at position 7 is Y; and the X at position 8 is G. VR112 comprises SEQ ID NO: 10 wherein the X at position 3 is N, the X at position 4 is V, the X at position 5 is P, the X at position 6 is V, the X at position 7 is Q, and the X at position 8 is G. VR115 comprises SEQ ID NO: 10 wherein the X at position 3 is D, the X at position 4 is I, the X at position 5 is P, the X at position 6 is T, the X at position 7 is K, and the X at position 8 is G. VR110 comprises SEQ ID NO: 10 wherein the X at position 3 is D, the X at position 4 is M, the X at position 5 is P, the X at position 6 is T, the X at position 7 is K, and the X at position 8 is G. VR24 comprises a LCDR1 set forth in SEQ ID NO: 17.

In one example, an antibody described herein comprises IgG4 or stabilized IgG4 constant regions. The term "stabilized IgG4 constant regions" will be understood to mean IgG4 constant regions that have been modified to reduce Fab arm exchange or the propensity to undergo Fab arm exchange or formation of a half-antibody or a propensity to form a half antibody. "Fab arm exchange" refers to a type of protein modification for human IgG4, in which an IgG4 heavy chain and attached light chain (half-molecule) is swapped for a heavy-light chain pair from another IgG4 molecule. Thus, IgG4 molecules may acquire two distinct Fab arms recognizing two distinct antigens (resulting in bispecific molecules). Fab arm exchange occurs naturally in vivo and can be induced in vitro by purified blood cells or reducing agents such as reduced glutathione. A "half antibody" forms when an IgG4 antibody dissociates to form two molecules each containing a single heavy chain and a single light chain.

In one example, a stabilized IgG4 constant region comprises a proline at position 241 of the hinge region according to the system of Kabat (Kabat et al., Sequences of Proteins of Immunological Interest Washington D.C. United States Department of Health and Human Services, 1987 and/or 1991). This position corresponds to position 228 of the hinge region according to the EU numbering system (Kabat et al., Sequences of Proteins of Immunological Interest Washington D.C. United States Department of Health and Human Services, 2001 and Edelman et al., Proc. Natl. Acad. Sci USA, 63, 78-85, 1969). In human IgG4, this residue is generally a serine. Following substitution of the serine for proline, the IgG4 hinge region comprises a sequence CPPC. In this regard, the skilled person will be aware that the "hinge region" is a proline-rich portion of an antibody heavy chain constant region that links the Fc and Fab regions that confers mobility on the two Fab arms of an antibody. The hinge region includes cysteine residues which are involved in inter-heavy chain disulfide bonds. It is generally defined as stretching from Glu226 to Pro243 of human IgG1 according to the numbering system of Kabat. Hinge regions of other IgG isotypes may be aligned with the IgG1 sequence by placing the first and last cysteine residues forming inter-heavy chain disulphide (S—S) bonds in the same positions (see for example WO 2010/080538).

Additional examples of stabilized IgG4 antibodies are antibodies in which arginine at position 409 in a heavy chain constant region of human IgG4 (according to the EU numbering system) is substituted with lysine, threonine, methionine, or leucine (e.g., as described in WO 2006/033386). The Fc region of the constant region may additionally or alternatively comprise a residue selected from the group consisting of: alanine, valine, glycine, isoleucine and leucine at the position corresponding to 405 (according to the EU numbering system). Optionally, the hinge region comprises a proline at position 241 (i.e., a CPPC sequence) (as described above).

In one example, the inhibitor of FXII of the present disclosure is antibody 3F7 or a chimeric, CDR grafted or humanized version thereof or an antigen binding fragment thereof.

In one example, antibody 3F7 comprises a $V_H$ comprising a sequence set forth in SEQ ID NO: 6 and a $V_L$ comprising a sequence set forth in SEQ ID NO: 7. In one example, antibody 3F7 comprises the complementary determining regions (CDRs) of the $V_H$ (SEQ ID NO: 6) and the $V_L$ (SEQ ID NO: 7).

For example, antibody 3F7 comprises a $V_H$ comprising a CDR1 set forth in SEQ ID NO: 8, a CDR2 set forth in SEQ ID NO: 9, a CDR3 set forth in SEQ ID NO: 11 and a $V_L$ comprising a CDR1 set forth in SEQ ID NO: 13, CDR2 set forth in SEQ ID NO: 14 and a CDR3 set forth in SEQ ID NO: 15.

In one example, the inhibitor of XII of the present disclosure is antibody VR115.

For example, antibody VR115 comprising a $V_H$ comprising a CDR1 set forth in SEQ ID NO: 8, a CDR2 set forth in SEQ ID NO: 10 wherein the X at position 3 is D, the X at position 4 is I, the X at position 5 is P, the X at position 6 is T, the X at position 7 is K, and the X at position 8 is G, and a CDR3 set forth in SEQ ID NO: 11 and a $V_L$ comprising a CDR1 set forth in SEQ ID NO: 13, CDR2 set forth in SEQ ID NO: 14 and a CDR3 set forth in SEQ ID NO: 15.

In one example, the antibody is a germlined antibody. A "germlined" antibody is an antibody where some or all somatic mutations that introduced changes into the framework residues are reversed to the original sequence present in the genome, e.g., a human genome. In this regard, not all changes need to be reversed in a germlined antibody.

For example, the antibody is a germlined VR115 antibody (gVR115).

For example, gVR115 comprises a $V_H$ comprising a sequence set forth in SEQ ID NO: 18 and a $V_L$ comprising a sequence set forth in SEQ ID NO: 19.

In one example, gVR115 comprises lambda light chain constant regions.

In one example, gVR115 comprises IgG4 or stabilized IgG4 constant regions. For example, the stabilized IgG4 constant regions comprise a proline at position 241 of the hinge region according to the system of Kabat (Kabat et al., Sequences of Proteins of Immunological Interest Washington D.C. United States Department of Health and Human Services, 1987 and/or 1991).

In one example, gVR115 comprises a heavy chain comprising a sequence set forth in SEQ ID NO: 20 and a light chain comprising a sequence set forth in SEQ ID NO: 21.

In another example, an antibody or protein comprising a variable region thereof is produced using a standard method, e.g., as is known in the art.

Factor XII Inhibitor Fusion Partners

In one example, the inhibitor of FXII is linked to a fusion partner. For example, the fusion partner comprises polyethylene glycol (PEG). In one example, the fusion partner comprises a half-life enhancing polypeptide (HLEPs).

Polyethylene Glycol (PEG)

In one example, the inhibitor of FXII is linked to a fusion partner. For example, the fusion partner comprises polyethylene glycol (PEG).

In one example, the fusion partner comprises mono- or poly- (e.g., 2-4) polyethylene glycol (PEG) moieties. For example, the mono- poly- (e.g., 2-4) polyethylene glycol (PEG) moieties extend in vivo half-lives of the FXII inhibitor.

Pegylation may be carried out by any of the pegylation reactions available. Exemplary methods for preparing pegylated protein products can generally include (a) reacting a polypeptide with polyethylene glycol (such as a reactive ester or aldehyde derivative of PEG) under conditions whereby the protein becomes attached to one or more PEG groups; and (b) obtaining the reaction product(s).

The skilled person will be aware of different PEG attachment methods which include, but are not limited to those described in e.g., EP 0 401 384; Malik et al., Exp. Hematol., 20:1028-1035 (1992); Francis, Focus on Growth Factors, 3(2):4-10 (1992); EP 0 154 316; EP 0 401 384; WO 92/16221; WO 95/34326; U.S. Pat. No. 5,252,714.

Half-Life Enhancing Polypeptides (HLEPs)

In one example, the inhibitor of FXII is linked to a fusion partner. For example, the fusion partner comprises a half-life enhancing polypeptide (HLEPs).

A variety of half-life enhancing polypeptides are known to the skilled artisan, and include, but are not limited to, those described herein.

Albumin Proteins and Variants Thereof

In one example, the half-life enhancing polypeptide is selected from the group consisting of albumin, afamin, alpha-fetoprotein, vitamin D binding protein, human albumin, an immunoglobulin, and an Fc of an IgG. For example, the half-life enhancing polypeptide is albumin or a variant thereof.

In one example, the half-life enhancing polypeptide is linked to the inhibitor of FXII via a linker. For example, the inhibitor of FXII is a fusion protein comprising human albumin linked to an inhibitor of FXII via a linker peptide.

In one example, an albumin variant is at least 10, or at least 20, or at least 40, or at least 50, or at least 60, or at least 70 amino acids long from a human albumin (HA) sequence (e.g., SEQ ID NO: 23).

In one example, an albumin variant is at least about 15, or at least 20, or at least about 25, or at least about 30, or at least about 50 or more contiguous amino acids from a human albumin (HA) sequence (e.g., SEQ ID NO: 23).

In one example, an albumin variant includes part or all of specific domains of HA. An albumin variant may include an amino acid substitution, deletion, or addition, either conservative or non-conservative substitution, wherein such changes do not substantially alter the active site, or active domain, which confers the therapeutic activities of the half-life enhancing polypeptides. These variants may share identity of about 70%, or about 75%, or about 80%, or about 85%, or about 90%, or about 91%, or about 92%, or about 93%, or about 94%, or about 95%, or about 96%, or about 97%, or about 98% or about 99% from a human albumin (HA) sequence.

In one example, an albumin variant is a fragment. In one example, the albumin variant comprises at least one domain of albumin and/or fragments of those domains. For example, the albumin variant comprises at least one of domain 1 (amino acids 1-194 of SEQ ID NO: 23), or domain 2 (amino acids 195-387 of SEQ ID NO: 23), or domain 3 (amino acids 388-585 of SEQ ID NO 23). In one example, the albumin variant comprises at least domains 1 and 2 (1-387 of SEQ ID NO: 23), or domains 2 and 3 (195-585 of SEQ ID NO: 23), or domains 1 and 3 (amino acids 1-194 and amino acids 388-585 of SEQ ID NO: 23).

Each domain is itself made up of two homologous sub-domains namely residues 1-105, 120-194, 195-291, 316-387, 388-491 and 512-585, of SEQ ID NO: 23, with flexible inter-subdomain linker regions comprising residues Lys106 to Glu119, Glu292 to Val315 and Glu492 to Ala511.

In one example, the albumin variant comprises at least one whole subdomain of albumin. For example, the albumin variant comprises residues 1-105, or residues 120-194, or residues 195-291, or residues 316-387, or residues 388-491, or residues 512-585 of SEQ ID NO: 23.

In one example, other proteins that are structurally or evolutionarily related to albumin ("albumin family proteins") may be used as HLEPs, including, but not limited to alpha-fetoprotein (WO 2005/024044; Beattie and Dugaiczyk, 20 Gene 415-422, 1982), afamin (Lichenstein et al. 269 (27) J. Biol. Chem. 18149-18154, 1994), and vitamin D binding protein (Cooke and David, 76 J. Clin. Invest. 2420-2424, 1985). The genes encoding these proteins represent a multigene cluster with structural and functional similarities mapping to the same chromosomal region in humans, mice, and rats. The structural similarity of the albumin family members suggests that they can be used as HLEPs. For example, alpha-fetoprotein has been claimed to extend the half-life of an attached therapeutic polypeptide in vivo (WO 2005/024044).

In one example, the half-life enhancing polypeptide is selected from the group consisting of alpha-fetoprotein and vitamin D binding protein. For example, the half-life enhancing polypeptide is alpha-fetoprotein. In one example, the half-life enhancing polypeptide is vitamin D binding protein.

In one example, the albumin family proteins or variants thereof are capable of stabilizing or prolonging therapeutic activity.

In one example, the albumin family proteins or variants thereof are used as HLEPs linked to a FXII or FXIIa inhibitor.

In one example, the albumin family proteins or variants thereof are derived from any vertebrate.

For example, the vertebrate is a mammal. In one example, the mammal is not a human, monkey, cow, sheep, or pig. In one example, the vertebrate is non-mammal. For example, the non-mammal is a hen or salmon.

In one example, the albumin variant comprises at least 10 amino acids in length. For example, the albumin variant comprises about 15, or about 20, or about 25, or about 30, or about 50 contiguous amino acids of the respective protein sequence from which they are derived. In one example, the albumin variant comprises part or all of specific domains of the respective proteins.

As discussed herein, albumin family member fusion proteins may include naturally occurring polymorphic variants.
Immunoglobulin In one example, the half-life enhancing polypeptide is an immunoglobulin (Ig).

As discussed above, the term "immunoglobulin" encompasses functional fragments and variants thereof, such as an Fc region or one or more Ig constant domains. In one example, the Ig comprises an Fc region or portions of the immunoglobulin constant domain(s). The constant region may be that of an IgM, IgG, IgD, IgA, or IgE immunoglobulin. In one example, the therapeutic polypeptide portion is connected to the Ig via the hinge region of the antibody or a peptide linker, which may be cleavable.

Methods for the fusion of therapeutic proteins to immunoglobulin constant regions to extend the therapeutic protein's half-life in vivo are known in the art and are described in e.g., US 2004/0087778, WO 2005/001025, WO 2005/063808, WO 2003/076567, WO 2005/000892, WO 2004/101740, U.S. Pat. No. 6,403,077.

In one example, the half-life enhancing polypeptide is an immunoglobulin region. For example, the immunoglobulin region is an Fc domain, or an Fc fragment of immunoglobulins, and/or variants thereof.

In one example, an inhibitor of FXII is fused to Fc domains or portions of immunoglobulin constant regions as HLEPs.

In one example, fusion proteins are prepared as recombinant molecules expressed in prokaryotic or eukaryotic host cells. For example, the fusion proteins are prepared in bacteria, or yeast, or plant, or animal (including insect) or human cell lines or in transgenic animals.

Methods of the expression of fusion proteins in prokaryotic or eukaryotic cells are known in the art and are described in e.g., WO 2008/098720.
Linkers In one example, the half-life enhancing polypeptide is linked to the inhibitor of FXII via a linker. For example, the linker is a linker peptide.

In one example, an intervening peptidic linker may be introduced between a therapeutic polypeptide and a HLEP.

In one example, the linker is a cleavable linker. For example, the linker is a cleavable linker if the HLEP has the potential to interfere with the therapeutic polypeptide's specific activity, for example, interference by steric hindrance.

In one example, the linker is cleavable by enzymes involved in coagulation. For example, the linker is cleavable by coagulation proteases of the intrinsic, extrinsic, or common coagulation pathway. Coagulation proteases of the intrinsic pathway include proteases in the contact activation pathway, e.g., FXIIa, FXIa, or FIXa. In one embodiment, the linker is cleaved by FXIIa. Proteases of the extrinsic pathway include proteases in the tissue factor pathway, for example, FVIIa. Proteases of the common pathway include proteases involved in the conversion of fibrinogen to fibrin, for example, FXa, FIIa, and FXIIIa.
Screening Assays Compounds that inhibit FXII signaling can be identified using techniques known in the art, e.g., as described below. Similarly, amounts of FXII inhibitors suitable for use in a method described herein can be determined or estimated using techniques known in the art, e.g., as described below.
FXIIa Amidolytic Activity For inhibitors that bind FXII an in vitro assay to determine the level of inhibitor of FXIIa amidolytic activity can be used.

In one example, the amidolytic activity can be measured by assay of the cleavage of FXII in the presence of an inhibitor of FXII and a buffer. For example, FXII is incubated in the presence of absence of an inhibitor of FXII or control. Following incubation and addition of a detection substrate, the amidolytic activity is spectrophotometrically determined as a change in optical density (i.e., colour change).

Compounds that are found to effectively inhibit amidolytic activity are identified as inhibitors of FXII.
In Vivo Animal Models In one example, an inhibitor of FXII is tested for therapeutic or prophylactic effects in an animal model of atherosclerosis.

Animal models for assessing the effect of an inhibitor of FXII on atherosclerotic lesions are known in the art and/or exemplified herein. Exemplary animal models include, for example, ApoE knockout (−/−) mouse model and a tandem stenosis mouse model.
ApoE Knockout Animal Model In one example, the animal model is an ApoE knockout mouse model.

For example, an inhibitor of FXII or control is administered to a model of atherosclerosis, for example, an ApoE−/− mouse model and the therapeutic efficacy of the inhibitor of FXII assessed.

In one example, the ApoE−/− (ApoE-KO) mice are treated with an inhibitor of FXII or control subcutaneously on alternate days. In one example, the ApoE−/− mice are fed a high-fat diet (HFD) containing 21% fat and 0.15% cholesterol.

In one example, the therapeutic efficacy of the inhibitor of FXII is assessed by histological and/or morphological analysis of atherosclerotic lesions.

Attenuation of atherosclerotic lesions in the animal model in the presence of an inhibitor of FXII compared to in the absence of an inhibitor of FXII indicates that the inhibitor of FXII is useful for treating atherosclerosis and stabilization of atherosclerotic plaques.

Tandem Stenosis Animal Model

In one example, the animal model is a tandem stenosis mouse model.

For example, an inhibitor of FXII or control is administered to a model of atherosclerosis, for example, a tandem stenosis mouse model and the therapeutic efficacy of the inhibitor of FXII assessed.

In one example, the mice are ApoE−/− knockout mice. In one example, the mice are fed a high-fat diet (HFD) containing 21% fat and 0.15% cholesterol.

In one example, the tandem stenosis is inserted into the right common carotid artery near the carotid artery bifurcation.

Attenuation of atherosclerotic lesions in the animal model in the presence of an inhibitor of FXII compared to in the absence of an inhibitor of FXII indicates that the inhibitor of FXII is useful for treating atherosclerosis and stabilization of atherosclerotic plaques.

Atherosclerotic Lesion Morphological Analysis

In one example, an inhibitor of FXII that attenuates development of atherosclerotic lesions is identified by performing histological analysis.

Suitable methods of morphological analysis are known in the art and include, for example, analysis of total lesion size, lipid area, necrotic core area, collagen accumulation, macrophage accumulation and expression of a number of markers including e.g., VCAM-1 and α-smooth muscle actin.

In one example, cryo-sections of atherosclerotic lesions from animal models are histologically stained with either Oil-red O (ORO) standard to detect lipids and total lesion area, Mayer's hematoxylin/eosin (H&E) to determine necrotic core areas (acellular areas) in atherosclerotic lesions, Picro-sirius Red to detect collagen. Quantification of histological samples for each segment is performed on sequential 6 μm sections obtained at 120 μm intervals. The percentage of the various plaque components is quantified as the positive area for each specific parameter divided by the total intimal plaque area. The necrotic core is defined as the total plaque area devoid of cellular tissue. Relative cap thickness is defined as the ratio of the cap thickness at the shoulder and mid-plaque region divided by maximal intimal thickness. Imaging to ORO positive and acellular regions within atherosclerotic lesions is carried out using light microscopy and cross sectional area of lipid deposition quantified using image analysis software (e.g., Optimas 6.2 Video Pro-32). For each mouse, lesion size is measured in at least 4 cross-sectional areas at 30 mm intervals.

Flow Cytometry

In one example, flow cytometric analysis is performed on for analysis of cell populations in the spleen, lymph node and blood.

In one example, B lymphocytes and non-B-lymphocyte populations in spleen, lymph node and blood are analysed with fluorochrome conjugated antibodies on a BD FACS Canto-II. For example, for analysis of B cells, PE-conjugated anti-CD19, APC-conjugated anti-CD5, and APC-Cy7-conjugated anti-CD11b Abs are used. For example, for analysis of non-B lymphocyte populations, Pacific Blue-conjugated anti-CD4, PerCP-conjugated anti-CD8a, FITC-conjugated anti-TCR-b, and PE-Cy7-conjugated anti-NK1.1 Abs are used.

Attenuation of atherosclerotic lesions in the animal model in the presence of an inhibitor of FXII compared to in the absence of an inhibitor of FXII indicates that the inhibitor of FXII is useful for treating atherosclerosis and stabilization of atherosclerotic plaques.

Pharmaceutical Compositions and Methods of Treatment

In some examples of the disclosure, the FXII inhibitor may have a purity of greater than 80%, or greater than 95%, 96%, 97%, 98%, or 99%. In one example, the FXII inhibitor may have a pharmaceutically pure state that is greater than 99.9% pure with respect to contaminating macromolecules, such as other proteins and nucleic acids, and may be free of infectious and pyrogenic agents.

A compound that inhibits FXII (syn. active ingredient) is useful for parenteral, topical, oral, or local administration, aerosol administration, or transdermal administration, for prophylactic or for therapeutic treatment. In one example, the inhibitor of FXII is administered parenterally, such as subcutaneously or intravenously. For example, the inhibitor of FXII is administered subcutaneously.

Formulation of a FXII inhibitor to be administered will vary according to the route of administration and formulation (e.g., solution, emulsion, capsule) selected. An appropriate pharmaceutical composition comprising a FXII inhibitor to be administered can be prepared in a physiologically acceptable carrier. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. A variety of appropriate aqueous carriers are known to the skilled artisan, including water, buffered water, buffered saline, polyols (e.g., glycerol, propylene glycol, liquid polyethylene glycol), dextrose solution and glycine. Intravenous vehicles can include various additives, preservatives, or fluid, nutrient or electrolyte replenishers (See, generally, Remington's Pharmaceutical Science, 16th Edition, Mack, Ed. 1980). The compositions can optionally contain pharmaceutically acceptable auxiliary substances as required to approximate physiological conditions such as pH adjusting and buffering agents and toxicity adjusting agents, for example, sodium acetate, sodium chloride, potassium chloride, calcium chloride and sodium lactate. Additional pharmaceutical additives include, e.g., mannitol, starch, glucose, lactose, sucrose, gelatin, malt, rice, flour, chalk, silica gel, sodium stearate, glycerol monostearate, talc, dried skim milk, and ethanol. The FXII inhibitor can be stored in the liquid stage or can be lyophilized for storage and reconstituted in a suitable carrier prior to use according to art-known lyophilization and reconstitution techniques.

Alternatively, or in addition, the carrier or excipient comprises a compound that enhances the activity of a FXII inhibitor and/or reduces inhibition of the FXII inhibitor, e.g., a protease inhibitor and/or a DNase inhibitor and/or an RNase inhibitor to thereby enhance the stability of the inhibitor.

The optimum concentration of the active ingredient(s) in the chosen medium can be determined empirically, according to procedures known to the skilled artisan, and will depend on the ultimate pharmaceutical formulation desired.

The dosage ranges for the administration of the FXII inhibitor of the disclosure are those large enough to produce the desired effect. For example, the composition comprises a therapeutically or prophylactically effective amount of the FXII inhibitor.

As used herein, the term "effective amount" shall be taken to mean a sufficient quantity of the FXII inhibitor to inhibit/reduce/prevent signaling of FXII and/or FXIIa in a subject. The skilled artisan will be aware that such an amount will vary depending on, for example, the FXII inhibitor and/or the particular subject and/or the type and/or the severity of atherosclerosis being treated. Accordingly, this term is not to be construed to limit the disclosure to a specific quantity, e.g., weight or number of FXII inhibitors.

The dosage should not be so large as to cause adverse side effects, such as hyper viscosity syndromes, pulmonary edema, congestive heart failure, and the like. Generally, the dosage will vary with the age, condition, sex and extent of the disease in the patient and can be determined by one of skill in the art. The dosage can be adjusted by the individual physician in the event of any complication.

Dosage can vary from about 0.1 mg/kg to about 300 mg/kg, e.g., from about 0.2 mg/kg to about 200 mg/kg, such as, from about 0.5 mg/kg to about 20 mg/kg, for example about 10 mg/kg in one or more dose administrations daily, for one or several days.

In some examples, the FXII inhibitor is administered at an initial (or loading) dose which is higher than subsequent (maintenance doses). For example, the FXII inhibitor is administered at an initial dose of between about 10 mg/kg to about 30 mg/kg. The FXII inhibitor is then administered at a maintenance dose of between about 0.0001 mg/kg to about 10 mg/kg. The maintenance doses may be administered every 7-100 days, such as, every 14 or 28 or 56 or 84 days.

In some examples, a dose escalation regime is used, in which a FXII inhibitor is initially administered at a lower dose than used in subsequent doses. This dosage regime is useful in the case of subject's initially suffering adverse events.

In the case of a subject that is not adequately responding to treatment, multiple doses in a week may be administered. Alternatively, or in addition, increasing doses may be administered.

A subject may be retreated with the FXII inhibitor, by being given more than one exposure or set of doses, such as at least about two exposures of the compound, for example, from about 2 to 60 exposures, and more particularly about 2 to 40 exposures, most particularly, about 2 to 20 exposures.

In another example, any retreatment may be given at defined intervals. For example, subsequent exposures may be administered at various intervals, such as, for example, about 24-28 weeks or 48-56 weeks or longer. For example, such exposures are administered at intervals each of about 24-26 weeks or about 38-42 weeks, or about 50-54 weeks.

A method of the present disclosure may also include co-administration of the at least one FXII inhibitor according to the disclosure together with the administration of another therapeutically effective agent for the prevention or treatment of atherosclerosis or atherosclerotic plaque rupture.

In one example, the FXII inhibitor of the disclosure is used in combination with at least one additional known compound which is currently being used or is in development for preventing or treating atherosclerosis. Examples of such known compounds include but are not limited to statins (e.g., Lovastatin, Pravastatin, Rosuvastatin, Simvastatin, Atorvastatin, and Fluvastatin) and blood thinning drugs (e.g., Asprin, Warfarin and Heparin).

As will be apparent from the foregoing, the present disclosure provides methods of concomitant therapeutic treatment of a subject, comprising administering to a subject in need thereof an effective amount of a first compound and a second compound, wherein said first agent is a FXII inhibitor, and the second agent is for the prevention or treatment of atherosclerosis.

As used herein, the term "concomitant" as in the phrase "concomitant therapeutic treatment" includes administering a first agent in the presence of a second agent. A concomitant therapeutic treatment method includes methods in which the first, second, third or additional agents are co-administered. A concomitant therapeutic treatment method also includes methods in which the first or additional agents are administered in the presence of a second or additional agent, wherein the second or additional agent, for example, may have been previously administered. A concomitant therapeutic treatment method may be executed step-wise by different actors. For example, one actor may administer to a subject a first agent and as a second actor may administer to the subject a second agent and the administering steps may be executed at the same time, or nearly the same time, or at distant times, so long as the first agent (and/or additional agents) are after administration in the presence of the second agent (and/or additional agents). The actor and the subject may be the same entity (e.g. a human).

In one example, the disclosure also provides a method for treating or preventing a atherosclerosis in a subject, the method comprising administering to the subject a first pharmaceutical composition comprising a FXII inhibitor of the disclosure and a second pharmaceutical composition comprising one or more additional compounds.

In one example, a method of the disclosure comprises administering a FXII inhibitor to a subject suffering from atherosclerosis and receiving another treatment (e.g., for diabetes and/or cholesterol).

Kits and Other Compositions of Matter

Another example of the disclosure provides kits containing a FXII inhibitor useful for the treatment of atherosclerosis as described above.

In one example, the kit comprises (a) a container comprising a FXII inhibitor as described herein, optionally in a pharmaceutically acceptable carrier or diluent; and (b) a package insert with instructions for treating atherosclerosis in a subject.

In accordance with this example of the disclosure, the package insert is on or associated with the container. Suitable containers include, for example, bottles, vials, syringes, etc. The containers may be formed from a variety of materials such as glass or plastic. The container holds or contains a composition that is effective for treating atherosclerosis and may have a sterile access port (for example, the container may be an intravenous solution bag or a vial having a stopper pierceable by a hypodermic injection needle). At least one active agent in the composition is the FXII inhibitor. The label or package insert indicates that the composition is used for treating a subject eligible for treatment, e.g., one having or predisposed to atherosclerosis, with specific guidance regarding dosing amounts and intervals of FXII inhibitor and any other medicament being provided. The kit may further comprise an additional container comprising a pharmaceutically acceptable diluent buffer, such as bacteriostatic water for injection (BWFI), phosphate-buffered saline, Ringer's solution, and/or dextrose solution. The kit may further include other materials desirable from a commercial and user standpoint, including other buffers, diluents, filters, needles, and syringes.

The kit optionally further comprises a container comprises a second medicament, wherein the FXII inhibitor is a first medicament, and which article further comprises instructions on the package insert for treating the subject with the second medicament, in an effective amount or another treatment for atherosclerosis. The second medicament may be any of those set forth above.

The present disclosure includes the following non-limiting examples.

EXAMPLES

Example 1: Factor XII Inhibitor Treatment Attenuates Progression and Development of Atherosclerotic Lesions Male ApoE−/− (ApoE-KO) mice with C57BL/6J background (6 weeks old) received anti-factor XIIa monoclonal antibody 3F7 (1 mg/kg) or IgG isotype control (MuBM4-MuG1K) subcutaneously on alternate days whilst being fed a high-fat diet (HFD) containing 21% fat and 0.15% cholesterol (SF00-219, Specialty Feeds, Western Australia) for 8 weeks.

Animals were sacrificed and a catheter was placed in the left ventricle for perfusion with 10 ml PBS, pH 7.4 under physiological pressure. After perfusion, the entire aortic arch with the brachiocephalic artery and the right and left carotid artery was embedded in optimal cutting temperature (OCT) compound (Sakura Finetechnical), frozen over liquid nitrogen and stored at −80° C. until sectioning.

Frozen carotid artery, aorta arch and aortic sinus sections of 6 μm thick transversal cryo sections were prepared using a cryostat (Zeiss MICROM HM 550). Sections were histologically stained with either Oil-red 0 (ORO) standard to detect lipids and total lesion area, Mayer's hematoxylin/eosin (H&E) to determine necrotic core areas (acellular areas) in atherosclerotic lesions, Picro-sirius Red to detect collagen. Quantification of histological samples for each segment was performed on sequential 6 μm sections obtained at 120 μm intervals. The percentage of the various plaque components was quantified as the positive area for each specific parameter divided by the total intimal plaque area. The necrotic core was defined as the total plaque area devoid of cellular tissue. Relative cap thickness was defined as the ratio of the cap thickness at the shoulder and mid-plaque region divided by maximal intimal thickness. Imaging to ORO positive and acellular regions within atherosclerotic lesions were carried out using light microscopy and cross sectional area of lipid deposition quantified using image analysis software (Optimas 6.2 Video Pro-32, Bedford Park, South Australia, Australia). For each mouse, lesion size was measured in 4 cross-sectional areas at 30 mm intervals.

Oil-Red O staining of atherosclerotic lesions in the aorta root revealed a highly significant reduction in total lesion size (FIG. 1A) and lipid accumulation (FIG. 1B) by 60% and 70%, respectively (all P<0.05).

As macrophages are a main component of atherosclerotic lesions, CD68 staining was performed, revealing that macrophage accumulation was also markedly reduced by 45% (P<0.05; FIG. 1O). Further evaluation of atherosclerotic lesions demonstrated a significant increase in collagen deposition in the lesion by 50% (P<0.05; FIG. 1D). H&E staining revealed a significant reduction in necrotic core area in the lesion by 52% (P<0.05; FIG. 1E). Atherosclerosis in the aortic arch was also studied, revealing a reduction in total lesion, lipid and macrophage accumulation by 50%, 47% and 60%, respectively (all P<0.05; FIG. 1F-H).

Flow cytometric analysis was performed for analysis of cell populations in the spleen, lymph node and blood. B lymphocytes and non-B-lymphocyte populations in spleen, LN and blood were analysed with fluorochrome conjugated antibodies (from BD Pharmingen, San Diego, Calif. unless otherwise stated) on a BD FACS Canto-II (BD Biosciences). For B cells, PE-conjugated anti-CD19, APC-conjugated anti-CD5, and APC-Cy7-conjugated anti-CD11 b Abs were used. For non-B lymphocyte populations, Pacific Blue-conjugated anti-CD4, PerCP-conjugated anti-CD8a, FITC-conjugated anti-TCR-b, and PE-Cy7-conjugated anti-NK1.1 Abs were used.

Figure 2:
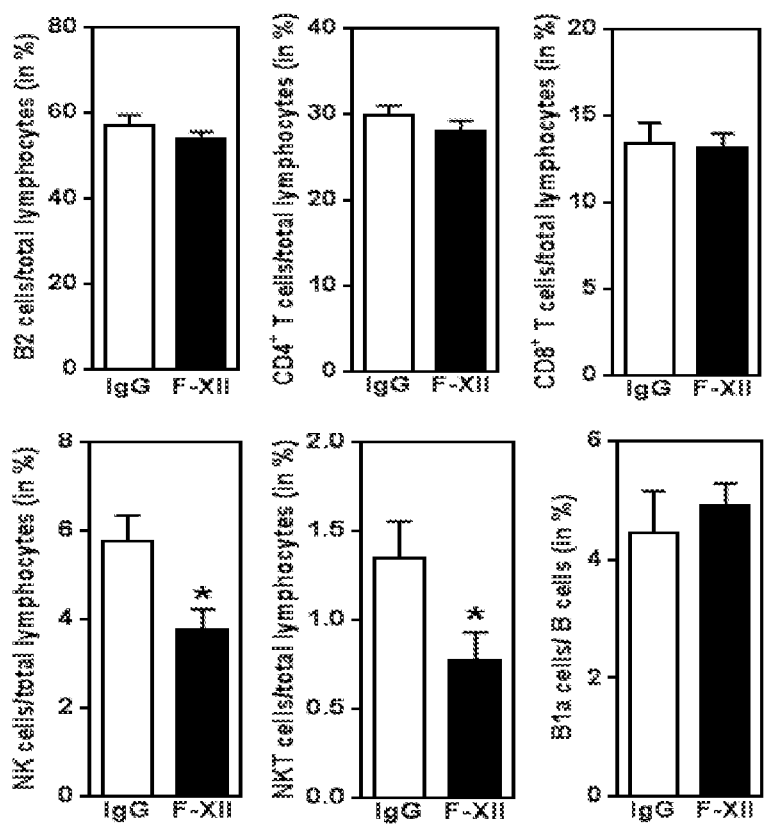
FIG. 2 is a graphical representation showing flow cytometric analysis of the lymphocyte profile in blood of mice with atherosclerotic lesions treated with anti-FXII antibody. Mean±SEM; n=6; *: $P<0.05$ compared to control, unpaired T-test.
Figure 3:
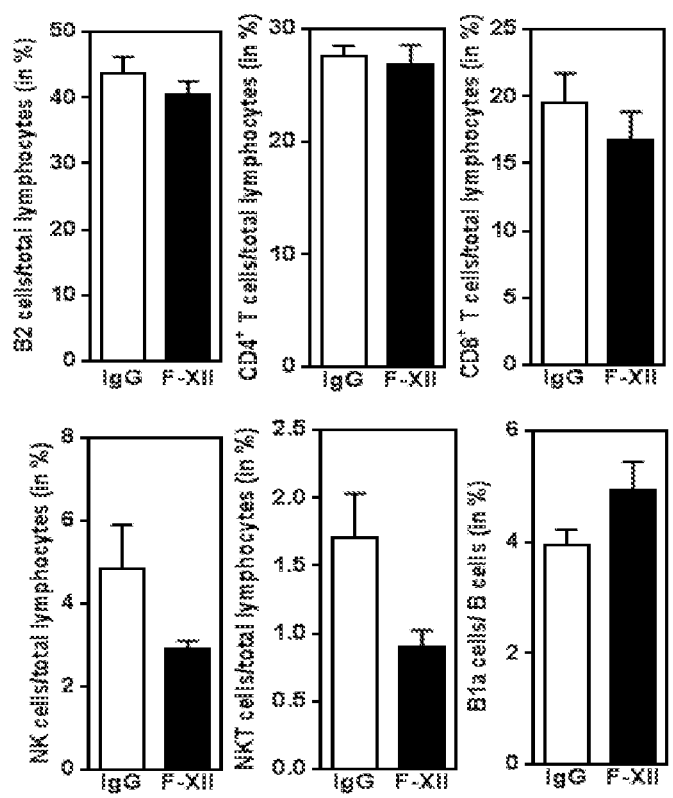
FIG. 3 is a graphical representation showing flow cytometric analysis of lymphocyte profile in lymph nodes of mice with atherosclerotic lesions treated with anti-FXII. Mean±SEM; n=6; *: $P<0.05$ compared to control, unpaired T-test.

Flow cytometric analysis of lymphocytic cell populations revealed that chronic treatment with a FXII inhibitor reduced NK and NKT cell populations in blood (FIG. 2) by 35% and 42%, respectively and in lymph node (FIG. 3) by 38% and 47%, respectively, without affecting other lymphocytes (P<0.05).

Figure 4:
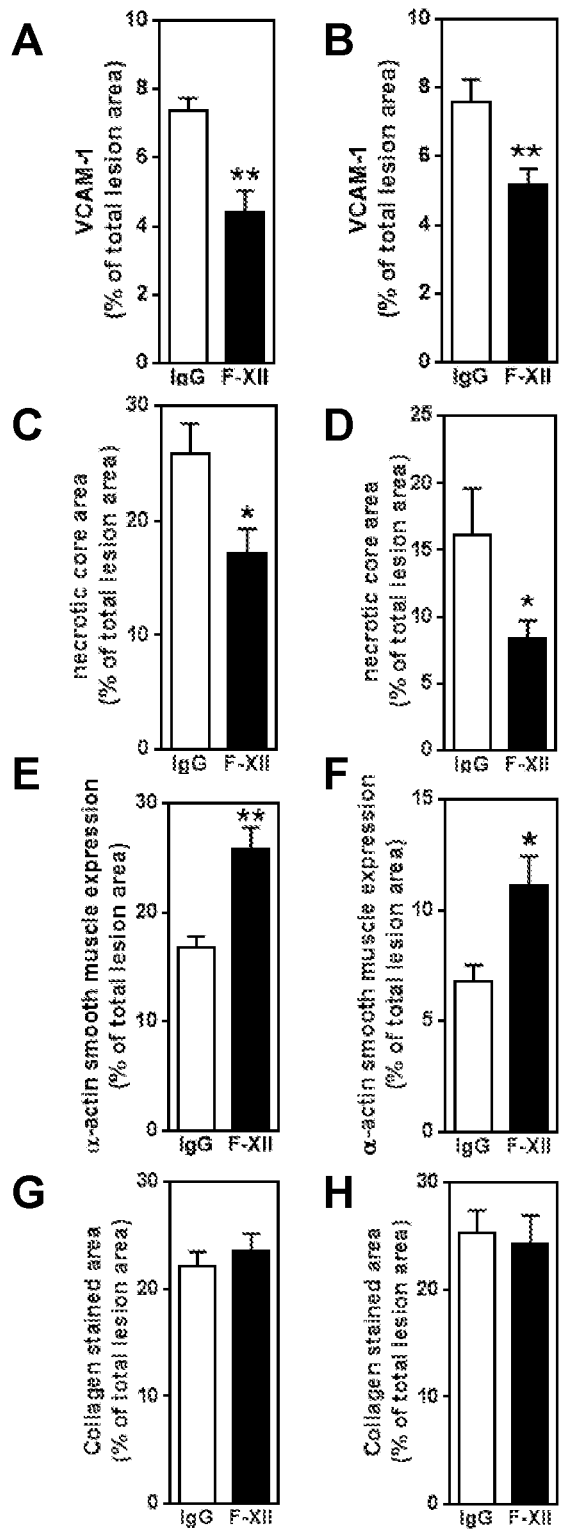
FIG. 4 is a graphical representation showing anti-FXII treatment reduces local inflammation and results in plaque stabilization of aortic sinus lesions (A, C, E, G) and aortic arch lesions (B, D, F, H). Aortic sinus lesions were analysed for VCAM-1 expression (A, B); necrotic core area (C, D), α-smooth muscle actin expression (E, F) and collagen accumulation (G, H). Mean±SEM; n=6; *: $P<0.05$ compared to control, unpaired T-test.

Example 2: Factor XII Inhibitor Treatment Reduces Arterial Inflammation and Increases Smooth Muscle Cell Number in Atherosclerotic Plaques To determine whether FXII inhibitor treatment reduced inflammation as a driving force of plaque development, the effect of chronic FXII inhibitor (3F7) treatment on the expression of vascular cell adhesion molecule-1 (VCAM-1; clone sc-1504, Santa Cruz) was investigated in atherosclerotic lesions of the aortic root and the aortic arch. A reduction of VCAM-1 expression was observed in the atherosclerotic lesions of the aortic root (43%) and the aortic arch (33%) (all P<0.05; FIG. 4A, B).

H&E staining also revealed a significant reduction in the size of the acellular area (necrotic core) in the atherosclerotic lesions of the aortic root and the aortic arch 33% and 50%, respectively, in 3F7 treated mice compared to the istotype IgG monoclonal antibody treated control group (all P<0.05; FIG. 4C, D).

In addition, we assessed the effect of FXII inhibitor treatment on the number of smooth muscle cells in atherosclerotic plaques by immunohistochemistry using α-smooth muscle actin antibody (clone 1A4; 1:100 dilution; Sigma Aldrich). FXII inhibitor treatment increased the number of smooth muscle cells in atherosclerotic plaques in the aortic root as well as in the aortic arch (all P<0.05; FIG. 4E, F). Interestingly, the collagen content in lesions neither in the aortic root nor in the aortic arch was changed (FIG. 4G, H).

In all immunohistochemical analysis detection was achieved by Vectastain ABC kit and the DAB substrate. Rat IgG2B control antibodies were used to validate the staining specificity of the applied rat antibody. Other isotype control antibodies (Goat IgG, rabbit IgG) were used for the validation of each immunostaining according to the primary antibodies. Expression of antigens was quantified using Optimus 6.2 VideoPro-32 and the stained segments were expressed as a percentage of the total plaque area.

Example 3: 3F7 Treatment Achieves Plaque Stabilization

To specifically address the question whether 3F7 has the potential to stabilize plaques, a recently developed unique mouse model of plaque instability/rupture was used.

In this model male ApoE−/− (ApoE-KO) mice were fed a high fat diet for 6 weeks to develop established atherosclerosis. At 12 weeks of age, 6 weeks after commencement of the high fat diet, ApoE-KO mice were anaesthetized by a ketamine (100 mg/kg) and xylazine (10 mg/kg) mixture through intraperitoneal injection. An incision was made in the neck and the right common carotid artery was dissected from circumferential connective tissues. A tandem stenosis with 150 μm (or 450 μm) outer diameters was introduced with the distal point 1 mm from the carotid artery bifurcation and the proximal point 3 mm from the distal stenosis. The stenosis diameter was obtained by placing a 6-0 blue braided polyester fibre suture around the carotid artery together with a 150- or 450-μm needle that was tied to it and later removed. Immediately after tandem stenosis surgery, mice were treated with the same regimen of either FXII inhibitor or IgG control while they were fed a high fat diet for a further 7 weeks. Animals and tissues were processed as described above in Examples 1 and 2.

Figure 5:
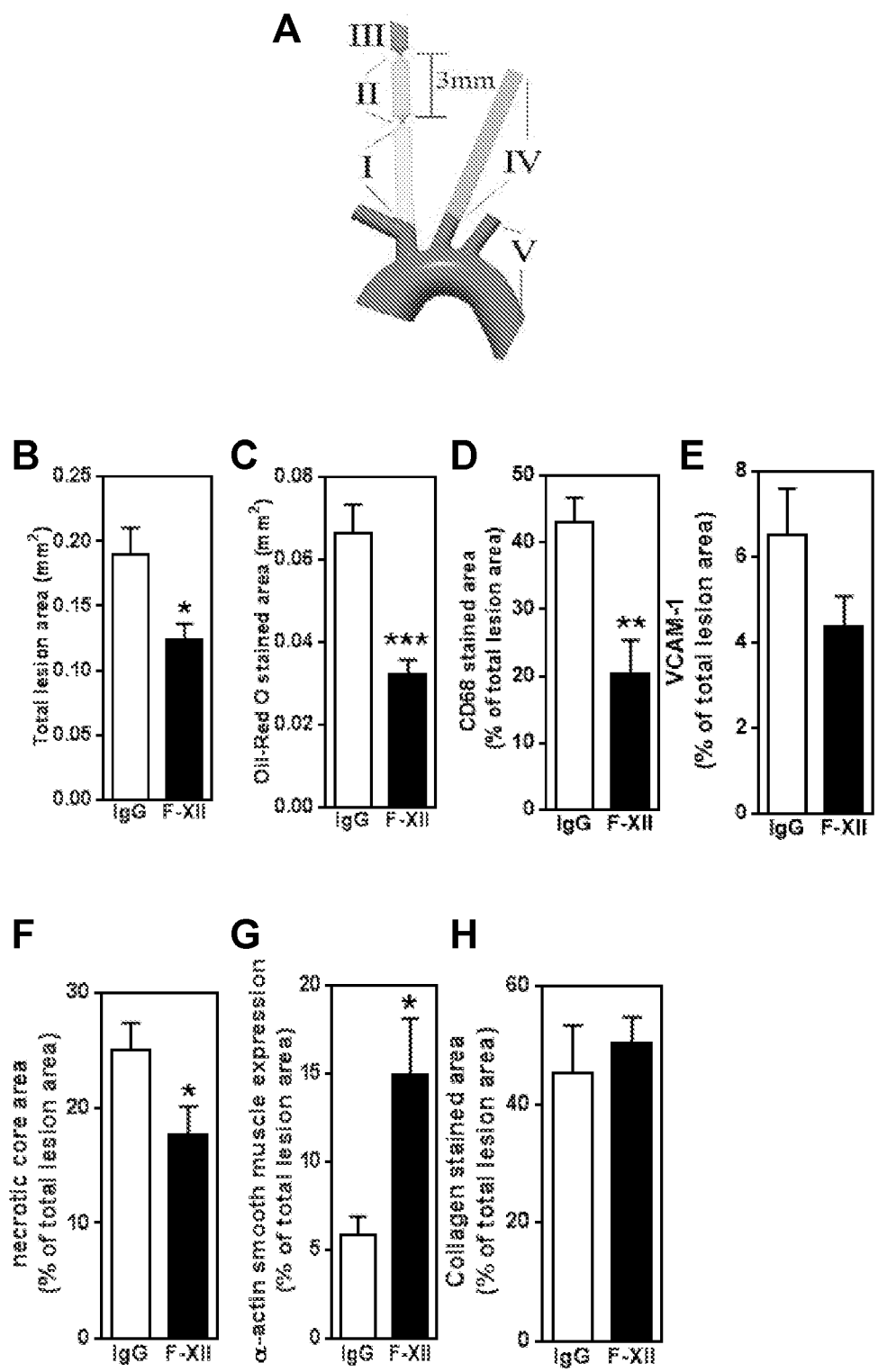
FIG. 5 is a graphical representation showing anti-FXII antibody treatment achieves plaque stabilization. Unstable atherosclerotic plaques were generated in segment I using the described tandem stenosis surgery (A) and analysed for atherosclerotic plaque area (B); lipid content (C); macrophage accumulation (D); VCAM-1 expression (E); necrotic core area (F); α-smooth muscle actin expression (G) and collagen accumulation (H). Mean±SEM, anti-FXIIa mAb: n=17, IgG isotype control: n=16, *: $P<0.05$ compared to control, unpaired T-test.

As shown in FIG. 5A, segment 1 represents the area of plaque instability. A reduction of total lesion size of 32% was observed in mice treated with the FXII inhibitor (FIG. 5B). Lipid and macrophage accumulation were also markedly reduced, by 52% and 53% respectively (all P<0.05; FIGS. 5C, D). VCAM-1 expression as a major measure of plaque inflammation was reduced by 30% in segment 1 of mice treated with 3F7 (FIG. 5E). Necrotic core size, again considered a marker of plaque instability, was reduced by 3F7 treatment by 32% (FIG. 5F). Most impressive was a significant increase in expression of smooth muscle cells expression in atherosclerotic lesion in segment 1 of nearly 2.5 fold (P<0.05; FIG. 5G). Interestingly, FXIIa inhibition by 3F7 did not result in a change of the collagen inhibition arguing for very specific effects on various plaque stabilizing mechanisms (FIG. 5H).

Example 4: Lipid Profile of Treated Animals

Cholesterol profiles (total cholesterol, high-density lipoprotein cholesterol, very-low-density lipoprotein/LDL cholesterol, and triglycerides) in plasma from ApoE−/− (ApoE-KO) mice either treated with 3F7 or control antibody were measured as described below.

Cholesterol

Cholesterol levels were measured by a standard commercial enzymatic assay using a Beckman Coulter LX20PRO Analyzer, with reagents and calibrators supplied by Beckman Coulter Diagnostics Australia.

CHOL reagent is used to measure cholesterol concentration by a timed-endpoint method. In the reaction, cholesterol esterase (CE) hydrolyzes cholesterol esters to free cholesterol and fatty acids. Free cholesterol is oxidized to cholestene-3-one and hydrogen peroxide by cholesterol oxidase (CO). Peroxidase catalyzes the reaction of hydrogen peroxide with 4-aminoantipyrine (4-AAP) and phenol to produce a colored quinoneimine product.

The SYNCHRON LX® System(s) automatically proportions the appropriate sample and reagent volumes into the cuvette. The ratio used is one part sample to 100 parts reagent. The system monitors the change in absorbance at 520 nanometers. This change in absorbance is directly proportional to the concentration of CHOL in the sample and is used by the System to calculate and express CHOL concentration.

HDL Cholesterol

HDL cholesterol was measured by a standard commercial enzymatic assay using a Beckman Coulter LX20PRO Analyser, with reagents and calibrators supplied by Beckman Coulter Diagnostics Australia.

This direct HDL Cholesterol method is a homogeneous assay without the need for any offline pretreatment or centrifugation steps. The method uses a detergent which solubilizes only the HDL lipoprotein particles and releases HDL cholesterol to react with cholesterol esterase and cholesterol oxidase in the presence of chromogens, to produce a color product. The same detergent also inhibits the reaction of the cholesterol enzymes with LDL, VLDL, and chylomicrons lipoproteins by adsorbing to their surfaces. A polyanion contained in the reagent enhances the selectivity for HDL cholesterol assay by complexing LDL, VLDL, and chylomicrons lipoproteins.

HDLD reagent was used to measure the cholesterol concentration by a timed-endpoint method. The SYNCHRON LX® System(s) automatically proportions the appropriate HDL cholesterol sample and reagent volumes into a cuvette. The ratio used is one part sample to 93 parts reagent. The System monitors the change in absorbance at 560 nanometers. This change in absorbance is directly proportional to the concentration of cholesterol in the sample and is used by the System to calculate and express the HDL-cholesterol concentration.

Triglycerides

Triglycerides were measured by a standard commercial enzymatic assay using a Beckman Coulter LX20PRO Analyser, with reagents and calibrators supplied by Beckman Coulter Diagnostics Australia.

Triglycerides GPO reagent was used to measure the triglycerides concentration by a timed endpoint method. Triglycerides in the sample were hydrolyzed to glycerol and free fatty acids by the action of lipase. A sequence of three coupled enzymatic steps using glycerol kinase (GK), glycerophosphate oxidase (GPO), and horseradish peroxidase (HPO) causes the oxidative coupling of 3,5-dichloro-2-hydroxybenze-nesulfonic acid (DHBS) with 4-aminoantipyrine to form a red quinoneimine dye.

The SYNCHRON LX® System(s) automatically proportions the appropriate sample and reagent volumes into the cuvette. The ratio used is one part sample to 100 parts reagent. The system monitors the change in absorbance at 520 nanometers. This change in absorbance is directly proportional to the concentration of TG in the sample and is used by the System to calculate and express the TG concentration.

Results

Results of the assays are shown in Table 2. These results show that an inhibitor of FXII (3F7) provides a beneficial effect in the context of atherosclerosis without changing cholesterol levels.

TABLE 2

| Experimental details | Body weight (gr) | Spleen weight (mgr) | Total Cholestrol (mmol/L) | VLDL/LDL Cholestrol (mmol/L) | Triglyceride (mmol/L) | HDL Cholestrol (mmol/L) |
|---|---|---|---|---|---|---|
| F-XII Ab. Treated TIS-ApoE −/− | 36.5 (±1.3) | 147 (±7.76) | 21.9 (±1.3) | 19.2 (±1.2) | 0.87 (±0.04) | 2.3 (±0.09) |
| IgG ctrl. Treated TIS-ApoE −/− | 38.4 (±1.4) | 138 (±7.61) | 24.3 (±1.05) | 21.4 (±0.9) | 0.88 (±0.04) | 2.4 (±0.13) |
| F-XII Ab. Treated HFD-ApoE −/− | 32.7 (±1.5) | 173 (±13.3) | 22.8 (±1.7) | 19.7 (±1.5) | 0.9 (±0.09) | 2.7 (±0.18) |
| IgG ctrl. Treated HFD-ApoE −/− | 34.5 (±1.7) | 149 (±8.79) | 24.9 (±1.8) | 21.4 (±1.6) | 1.1 (±0.12) | 2.9 (±0.24) |

The invention claimed is:

1. A method for treating atherosclerosis in a subject, comprising administering to the subject an effective amount of an inhibitor of Factor XII (FXII), wherein the inhibitor of FXII is an anti-FXII antibody or antigen binding fragment thereof comprising:
   (i) a $V_H$ comprising the polypeptide sequence set forth in SEQ ID NO: 18 and a $V_L$ comprising the polypeptide sequence set forth in SEQ ID NO: 19; or
   (ii) a heavy chain comprising the polypeptide sequence set forth in SEQ ID NO: 20 and a light chain comprising the polypeptide sequence set forth in SEQ ID NO: 21.

2. The method of claim 1, wherein the method (i) reduces atherosclerotic plaques in the subject, (ii) stabilizes vulnerable atherosclerotic plaques in the subject, and/or (iii) reduces the risk of atherosclerotic plaque rupture in the subject.

3. The method of claim 1, wherein the anti-FXII antibody or antigen binding fragment thereof is an IgG antibody.

4. The method of claim 1, wherein the inhibitor of FXII is linked to a fusion partner comprising polyethylene glycol (PEG) or a half-life enhancing polypeptide, and wherein the half-life enhancing polypeptide is selected from the group consisting of albumin, afamin, alpha-fetoprotein, vitamin D binding protein, and human albumin.

5. The method of claim 4, wherein the half-life enhancing polypeptide is linked to the inhibitor of FXII via a linker.

6. The method of claim 3, wherein the inhibitor of FXII is a fusion protein comprising human albumin linked to an inhibitor of FXII via a linker peptide.

7. The method of claim 1, wherein the inhibitor of FXII is administered to the subject intravenously, subcutaneously, or intrathecally.

8. The method of claim 1, wherein the inhibitor of FXII is administered to the subject:
   (i) in a single dose;
   (ii) in a plurality of doses; or
   (iii) as a continuous dose.

9. The method of claim 1, wherein the inhibitor of FXII is administered to the subject at a concentration of from about 0.01 to about 100 mg/kg body weight.

10. The method of claim 1, wherein the subject suffers from diabetes and/or obesity.

11. The method of claim 1, wherein the inhibitor of FXII is administered to the subject at a concentration of from about 1 to about 20 mg/kg body weight.

12. An anti-Factor XII (FXII) antibody or antigen binding fragment thereof, comprising:
   (i) a $V_H$ comprising the polypeptide sequence set forth in SEQ ID NO: 18 and a $V_L$ comprising the polypeptide sequence set forth in SEQ ID NO: 19; or
   (ii) a heavy chain comprising the polypeptide sequence set forth in SEQ ID NO: 20 and a light chain comprising the polypeptide sequence set forth in SEQ ID NO: 21.

13. A kit comprising:
   (a) at least one inhibitor of FXII comprising the anti-FXII antibody or antigen binding fragment thereof of claim 12;
   (b) instructions for using the kit for treating or preventing atherosclerosis in a subject; and
   (c) optionally, at least one further therapeutically active compound or drug.

* * * * *

SEQUENCE LISTING

<160> NUMBER OF SEQ ID NOS: 25

<210> SEQ ID NO 1
<211> LENGTH: 48
<212> TYPE: PRT
<213> ORGANISM: Artificial Sequence
<220> FEATURE:
<223> OTHER INFORMATION: amino acid sequence of wild-type Infestin-4

<400> SEQUENCE: 1

Glu Val Arg Asn Pro Cys Ala Cys Phe Arg Asn Tyr Val Pro Val Cys
1               5                   10                  15

Gly Ser Asp Gly Lys Thr Tyr Gly Asn Pro Cys Met Leu Asn Cys Ala
            20                  25                  30

Ala Gln Thr Lys Val Pro Gly Leu Lys Leu Val His Glu Gly Arg Cys
        35                  40                  45

<210> SEQ ID NO 2
<211> LENGTH: 56
<212> TYPE: PRT
<213> ORGANISM: Artificial Sequence
<220> FEATURE:
<223> OTHER INFORMATION: amino acid sequence of wild-type SPINK-1

<400> SEQUENCE: 2

Asp Ser Leu Gly Arg Glu Ala Lys Cys Tyr Asn Glu Leu Asn Gly Cys
1               5                   10                  15

Thr Lys Ile Tyr Asp Pro Val Cys Gly Thr Asp Gly Asn Thr Tyr Pro
            20                  25                  30

Asn Glu Cys Val Leu Cys Phe Glu Asn Arg Lys Arg Gln Thr Ser Ile
        35                  40                  45

Leu Ile Gln Lys Ser Gly Pro Cys
    50                  55

<210> SEQ ID NO 3
<211> LENGTH: 53
<212> TYPE: PRT
<213> ORGANISM: Artificial Sequence
<220> FEATURE:
<223> OTHER INFORMATION: SPINK-1 mutant K1

<400> SEQUENCE: 3

Asp Ser Leu Gly Arg Glu Val Arg Asn Pro Cys Ala Cys Phe Arg Asn
1               5                   10                  15

Tyr Val Pro Val Cys Gly Thr Asp Gly Asn Thr Tyr Pro Asn Glu Cys
            20                  25                  30

Val Leu Cys Phe Glu Asn Arg Lys Arg Gln Thr Ser Ile Leu Ile Gln
        35                  40                  45

Lys Ser Gly Pro Cys
    50

<210> SEQ ID NO 4
<211> LENGTH: 53
<212> TYPE: PRT
<213> ORGANISM: Artificial Sequence
<220> FEATURE:
<223> OTHER INFORMATION: SPINK-1 mutant K2

<400> SEQUENCE: 4

Asp Ser Leu Gly Arg Glu Val Arg Asn Pro Cys Ala Cys Phe Arg Asn
1               5                   10                  15

Tyr Val Pro Val Cys Gly Thr Asp Gly Asn Thr Tyr Gly Asn Glu Cys

```
                    20                  25                  30

Met Leu Cys Ala Glu Asn Arg Lys Arg Gln Thr Ser Ile Leu Ile Gln
            35                  40                  45

Lys Glu Gly Pro Cys
        50
```

<210> SEQ ID NO 5
<211> LENGTH: 54
<212> TYPE: PRT
<213> ORGANISM: Artificial Sequence
<220> FEATURE:
<223> OTHER INFORMATION: SPINK-1 mutant K3

<400> SEQUENCE: 5

```
Asp Ser Leu Gly Arg Glu Val Arg Asn Pro Cys Ala Cys Phe Arg Asn
1               5                   10                  15

Tyr Val Pro Val Cys Gly Thr Asp Gly Asn Thr Tyr Gly Asn Glu Cys
                20                  25                  30

Met Leu Asn Cys Ala Glu Asn Arg Lys Arg Gln Thr Ser Ile Leu Ile
            35                  40                  45

Gln Lys Glu Gly Pro Cys
        50
```

<210> SEQ ID NO 6
<211> LENGTH: 129
<212> TYPE: PRT
<213> ORGANISM: Artificial Sequence
<220> FEATURE:
<223> OTHER INFORMATION: amino acid sequence from a VH of an anti-FXII
      antibody

<400> SEQUENCE: 6

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
                20                  25                  30

Ile Met Gln Trp Val Arg Gln Ala Pro Gly Lys Gly Leu Glu Trp Val
            35                  40                  45

Ser Gly Ile Arg Pro Ser Gly Gly Thr Thr Val Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Leu Pro Arg Ser Gly Tyr Leu Ile Ser Pro His Tyr Tyr
            100                 105                 110

Tyr Tyr Ala Leu Asp Val Trp Gly Gln Gly Thr Thr Val Thr Val Ser
        115                 120                 125

Ser
```

<210> SEQ ID NO 7
<211> LENGTH: 110
<212> TYPE: PRT
<213> ORGANISM: Artificial Sequence
<220> FEATURE:
<223> OTHER INFORMATION: amino acid sequence from a VL of an anti-FXII
      antibody

<400> SEQUENCE: 7

```
Gln Ser Glu Leu Thr Gln Pro Pro Ser Ala Ser Gly Thr Pro Gly Gln
```

```
                1               5                   10                  15
Arg Val Thr Ile Ser Cys Ser Gly Ser Ser Asn Ile Gly Arg Asn
                20                  25                  30

Tyr Val Tyr Trp Tyr Gln Gln Val Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Val Ile Ser Gly Leu Arg
65                  70                  75                  80

Ser Glu Asp Glu Ala Asp Tyr Tyr Cys Ala Ala Trp Asp Ala Ser Leu
                85                  90                  95

Arg Gly Val Phe Gly Gly Gly Thr Lys Leu Thr Val Leu Gly
                100                 105                 110
```

```
<210> SEQ ID NO 8
<211> LENGTH: 5
<212> TYPE: PRT
<213> ORGANISM: Artificial Sequence
<220> FEATURE:
<223> OTHER INFORMATION: amino acid sequence from a VH CDR1 of an
      anti-FXII antibody

<400> SEQUENCE: 8

Lys Tyr Ile Met Gln
1               5
```

```
<210> SEQ ID NO 9
<211> LENGTH: 17
<212> TYPE: PRT
<213> ORGANISM: Artificial Sequence
<220> FEATURE:
<223> OTHER INFORMATION: amino acid sequence from a VH CDR2 of an
      anti-FXII antibody

<400> SEQUENCE: 9

Gly Ile Arg Pro Ser Gly Gly Thr Thr Val Tyr Ala Asp Ser Val Lys
1               5                   10                  15

Gly
```

```
<210> SEQ ID NO 10
<211> LENGTH: 17
<212> TYPE: PRT
<213> ORGANISM: Artificial Sequence
<220> FEATURE:
<223> OTHER INFORMATION: amino acid sequence from a VH CDR2 of an
      anti-FXII antibody
<220> FEATURE:
<221> NAME/KEY: X
<222> LOCATION: (3)..(3)
<223> OTHER INFORMATION: R or N or D
<220> FEATURE:
<221> NAME/KEY: X
<222> LOCATION: (4)..(4)
<223> OTHER INFORMATION: P or V or I or M
<220> FEATURE:
<221> NAME/KEY: X
<222> LOCATION: (5)..(5)
<223> OTHER INFORMATION: S or P or A
<220> FEATURE:
<221> NAME/KEY: X
<222> LOCATION: (6)..(6)
<223> OTHER INFORMATION: G or L or V or T
<220> FEATURE:
<221> NAME/KEY: misc_feature
<222> LOCATION: (7)..(7)
<223> OTHER INFORMATION: Xaa can be any naturally occurring amino acid
<220> FEATURE:
```

```
<221> NAME/KEY: X
<222> LOCATION: (8)..(8)
<223> OTHER INFORMATION: G or S

<400> SEQUENCE: 10

Gly Ile Xaa Xaa Xaa Xaa Xaa Xaa Thr Val Tyr Ala Asp Ser Val Lys
1               5                   10                  15

Gly

<210> SEQ ID NO 11
<211> LENGTH: 20
<212> TYPE: PRT
<213> ORGANISM: Artificial Sequence
<220> FEATURE:
<223> OTHER INFORMATION: amino acid sequence from a VH CDR3 of an
      anti-FXII antibody

<400> SEQUENCE: 11

Ala Leu Pro Arg Ser Gly Tyr Leu Ile Ser Pro His Tyr Tyr Tyr Tyr
1               5                   10                  15

Ala Leu Asp Val
            20

<210> SEQ ID NO 12
<211> LENGTH: 20
<212> TYPE: PRT
<213> ORGANISM: Artificial Sequence
<220> FEATURE:
<223> OTHER INFORMATION: amino acid sequence from a VH CDR3 of an
      anti-FXII antibody
<220> FEATURE:
<221> NAME/KEY: X
<222> LOCATION: (9)..(9)
<223> OTHER INFORMATION: I or M or V
<220> FEATURE:
<221> NAME/KEY: X
<222> LOCATION: (10)..(10)
<223> OTHER INFORMATION: S or K
<220> FEATURE:
<221> NAME/KEY: X
<222> LOCATION: (11)..(11)
<223> OTHER INFORMATION: P or K or T or H
<220> FEATURE:
<221> NAME/KEY: X
<222> LOCATION: (12)..(12)
<223> OTHER INFORMATION: H or N or G or Q

<400> SEQUENCE: 12

Ala Leu Pro Arg Ser Gly Tyr Leu Xaa Xaa Xaa Xaa Tyr Tyr Tyr Tyr
1               5                   10                  15

Ala Leu Asp Val
            20

<210> SEQ ID NO 13
<211> LENGTH: 13
<212> TYPE: PRT
<213> ORGANISM: Artificial Sequence
<220> FEATURE:
<223> OTHER INFORMATION: amino acid sequence from a VL CDR1 of an
      anti-FXII antibody

<400> SEQUENCE: 13

Ser Gly Ser Ser Ser Asn Ile Gly Arg Asn Tyr Val Tyr
1               5                   10

<210> SEQ ID NO 14
<211> LENGTH: 7
<212> TYPE: PRT
```

```
<213> ORGANISM: Artificial Sequence
<220> FEATURE:
<223> OTHER INFORMATION: amino acid sequence from a VL CDR2 of an
      anti-FXII antibody

<400> SEQUENCE: 14

Ser Asn Asn Gln Arg Pro Ser
1               5

<210> SEQ ID NO 15
<211> LENGTH: 10
<212> TYPE: PRT
<213> ORGANISM: Artificial Sequence
<220> FEATURE:
<223> OTHER INFORMATION: amino acid sequence from a VL CDR3 of an
      anti-FXII antibody

<400> SEQUENCE: 15

Ala Ala Trp Asp Ala Ser Leu Arg Gly Val
1               5                   10

<210> SEQ ID NO 16
<211> LENGTH: 10
<212> TYPE: PRT
<213> ORGANISM: Artificial Sequence
<220> FEATURE:
<223> OTHER INFORMATION: amino acid sequence from a VL CDR3 of an
      anti-FXII antibody
<220> FEATURE:
<221> NAME/KEY: X
<222> LOCATION: (2)..(2)
<223> OTHER INFORMATION: A or S
<220> FEATURE:
<221> NAME/KEY: X
<222> LOCATION: (4)..(4)
<223> OTHER INFORMATION: D or Y or E or T or W or S
<220> FEATURE:
<221> NAME/KEY: X
<222> LOCATION: (5)..(5)
<223> OTHER INFORMATION: A or N or I or L or V or P or Q or E
<220> FEATURE:
<221> NAME/KEY: X
<222> LOCATION: (6)..(6)
<223> OTHER INFORMATION: S or D or P or E or Q or R
<220> FEATURE:
<221> NAME/KEY: X
<222> LOCATION: (7)..(7)
<223> OTHER INFORMATION: L or V
<220> FEATURE:
<221> NAME/KEY: X
<222> LOCATION: (9)..(9)
<223> OTHER INFORMATION: G or L or K
<220> FEATURE:
<221> NAME/KEY: X
<222> LOCATION: (10)..(10)
<223> OTHER INFORMATION: V or A or D or T or M or G

<400> SEQUENCE: 16

Ala Xaa Trp Xaa Xaa Xaa Xaa Arg Xaa Xaa
1               5                   10

<210> SEQ ID NO 17
<211> LENGTH: 13
<212> TYPE: PRT
<213> ORGANISM: Artificial Sequence
<220> FEATURE:
<223> OTHER INFORMATION: amino acid sequence from a VL CDR1 of an
      anti-FXII antibody

<400> SEQUENCE: 17

Ser Gly Ser Ser Glu Met Thr Val His His Tyr Val Tyr
1               5                   10
```

<210> SEQ ID NO 18
<211> LENGTH: 129
<212> TYPE: PRT
<213> ORGANISM: artificial sequence
<220> FEATURE:
<223> OTHER INFORMATION: VH of anti-FXII antibody gVR115

<400> SEQUENCE: 18

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Ile Met Gln Trp Val Arg Gln Ala Pro Gly Lys Gly Leu Glu Trp Val
        35                  40                  45

Ser Gly Ile Asp Ile Pro Thr Lys Gly Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Leu Pro Arg Ser Gly Tyr Leu Ile Ser Pro His Tyr Tyr
            100                 105                 110

Tyr Tyr Ala Leu Asp Val Trp Gly Gln Gly Thr Thr Val Thr Val Ser
        115                 120                 125

Ser
```

<210> SEQ ID NO 19
<211> LENGTH: 110
<212> TYPE: PRT
<213> ORGANISM: artificial sequence
<220> FEATURE:
<223> OTHER INFORMATION: VL of anti-FXII antibody gVR115

<400> SEQUENCE: 19

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Arg Asn
            20                  25                  30

Tyr Val Tyr Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Ala Ser Leu
                85                  90                  95

Arg Gly Val Phe Gly Gly Gly Thr Lys Leu Thr Val Leu Gly
            100                 105                 110
```

<210> SEQ ID NO 20
<211> LENGTH: 456
<212> TYPE: PRT
<213> ORGANISM: artificial sequence
<220> FEATURE:
<223> OTHER INFORMATION: heavy chain of anti-FXII antibody gVR1

<400> SEQUENCE: 20

```
Glu Val Gln Leu Leu Glu Ser Gly Gly Gly Leu Val Gln Pro Gly Gly
```

-continued

```
1               5                   10                  15
Ser Leu Arg Leu Ser Cys Ala Ala Ser Gly Phe Thr Phe Ser Lys Tyr
             20                  25                  30

Ile Met Gln Trp Val Arg Gln Ala Pro Gly Lys Gly Leu Glu Trp Val
             35                  40                  45

Ser Gly Ile Asp Ile Pro Thr Lys Gly Thr Val Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ala Leu Pro Arg Ser Gly Tyr Leu Ile Ser Pro His Tyr Tyr
            100                 105                 110

Tyr Tyr Ala Leu Asp Val Trp Gly Gln Gly Thr Thr Val Thr Val Ser
            115                 120                 125

Ser Ala Ser Thr Lys Gly Pro Ser Val Phe Pro Leu Ala Pro Cys Ser
        130                 135                 140

Arg Ser Thr Ser Glu Ser Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Lys
        195                 200                 205

Thr Tyr Thr Cys Asn Val Asp His Lys Pro Ser Asn Thr Lys Val Asp
210                 215                 220

Lys Arg Val Glu Ser Lys Tyr Gly Pro Pro Cys Pro Pro Cys Pro Ala
225                 230                 235                 240

Pro Glu Phe Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser Gln Glu Asp Pro Glu Val Gln Phe Asn Trp Tyr Val
        275                 280                 285

Asp Gly Val Glu Val His Asn Ala Lys Thr Lys Pro Arg Glu Glu Gln
    290                 295                 300

Phe Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Gly
                325                 330                 335

Leu Pro Ser Ser Ile Glu Lys Thr Ile Ser Lys Ala Lys Gly Gln Pro
            340                 345                 350

Arg Glu Pro Gln Val Tyr Thr Leu Pro Pro Ser Gln Glu Met Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Arg Leu Thr Val Asp Lys Ser Arg Trp Gln Glu Gly Asn Val Phe
            420                 425                 430
```

```
Ser Cys Ser Val Met His Glu Ala Leu His Asn His Tyr Thr Gln Lys
        435                 440                 445

Ser Leu Ser Leu Ser Leu Gly Lys
    450                 455
```

<210> SEQ ID NO 21
<211> LENGTH: 215
<212> TYPE: PRT
<213> ORGANISM: artificial sequence
<220> FEATURE:
<223> OTHER INFORMATION: light chain of anti-FXII antibody gVR115

<400> SEQUENCE: 21

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Arg Asn
            20                  25                  30

Tyr Val Tyr Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Ala Ser Leu
                85                  90                  95

Arg Gly Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215
```

<210> SEQ ID NO 22
<211> LENGTH: 615
<212> TYPE: PRT
<213> ORGANISM: Homo sapiens

<400> SEQUENCE: 22

```
Met Arg Ala Leu Leu Leu Gly Phe Leu Leu Val Ser Leu Glu Ser
1               5                   10                  15

Thr Leu Ser Ile Pro Pro Trp Glu Ala Pro Lys Glu His Lys Tyr Lys
            20                  25                  30

Ala Glu Glu His Thr Val Val Leu Thr Val Thr Gly Glu Pro Cys His
        35                  40                  45

Phe Pro Phe Gln Tyr His Arg Gln Leu Tyr His Lys Cys Thr His Lys
    50                  55                  60
```

-continued

```
Gly Arg Pro Gly Pro Gln Pro Trp Cys Ala Thr Pro Asn Phe Asp
 65                  70                  75                  80

Gln Asp Gln Arg Trp Gly Tyr Cys Leu Glu Pro Lys Lys Val Lys Asp
                 85                  90                  95

His Cys Ser Lys His Ser Pro Cys Gln Lys Gly Gly Thr Cys Val Asn
            100                 105                 110

Met Pro Ser Gly Pro His Cys Leu Cys Pro Gln His Leu Thr Gly Asn
        115                 120                 125

His Cys Gln Lys Glu Lys Cys Phe Glu Pro Gln Leu Leu Arg Phe Phe
    130                 135                 140

His Lys Asn Glu Ile Trp Tyr Arg Thr Glu Gln Ala Ala Val Ala Arg
145                 150                 155                 160

Cys Gln Cys Lys Gly Pro Asp Ala His Cys Gln Arg Leu Ala Ser Gln
                165                 170                 175

Ala Cys Arg Thr Asn Pro Cys Leu His Gly Gly Arg Cys Leu Glu Val
            180                 185                 190

Glu Gly His Arg Leu Cys His Cys Pro Val Gly Tyr Thr Gly Ala Phe
        195                 200                 205

Cys Asp Val Asp Thr Lys Ala Ser Cys Tyr Asp Gly Arg Gly Leu Ser
    210                 215                 220

Tyr Arg Gly Leu Ala Arg Thr Thr Leu Ser Gly Ala Pro Cys Gln Pro
225                 230                 235                 240

Trp Ala Ser Glu Ala Thr Tyr Arg Asn Val Thr Ala Glu Gln Ala Arg
                245                 250                 255

Asn Trp Gly Leu Gly Gly His Ala Phe Cys Arg Asn Pro Asp Asn Asp
            260                 265                 270

Ile Arg Pro Trp Cys Phe Val Leu Asn Arg Asp Arg Leu Ser Trp Glu
        275                 280                 285

Tyr Cys Asp Leu Ala Gln Cys Gln Thr Pro Thr Gln Ala Ala Pro Pro
    290                 295                 300

Thr Pro Val Ser Pro Arg Leu His Val Pro Leu Met Pro Ala Gln Pro
305                 310                 315                 320

Ala Pro Pro Lys Pro Gln Pro Thr Thr Arg Thr Pro Pro Gln Ser Gln
                325                 330                 335

Thr Pro Gly Ala Leu Pro Ala Lys Arg Glu Gln Pro Pro Ser Leu Thr
            340                 345                 350

Arg Asn Gly Pro Leu Ser Cys Gly Gln Arg Leu Arg Lys Ser Leu Ser
        355                 360                 365

Ser Met Thr Arg Val Val Gly Gly Leu Val Ala Leu Arg Gly Ala His
    370                 375                 380

Pro Tyr Ile Ala Ala Leu Tyr Trp Gly His Ser Phe Cys Ala Gly Ser
385                 390                 395                 400

Leu Ile Ala Pro Cys Trp Val Leu Thr Ala Ala His Cys Leu Gln Asp
                405                 410                 415

Arg Pro Ala Pro Glu Asp Leu Thr Val Val Leu Gly Gln Glu Arg Arg
            420                 425                 430

Asn His Ser Cys Glu Pro Cys Gln Thr Leu Ala Val Arg Ser Tyr Arg
        435                 440                 445

Leu His Glu Ala Phe Ser Pro Val Ser Tyr Gln His Asp Leu Ala Leu
    450                 455                 460

Leu Arg Leu Gln Glu Asp Ala Asp Gly Ser Cys Ala Leu Leu Ser Pro
465                 470                 475                 480

Tyr Val Gln Pro Val Cys Leu Pro Ser Gly Ala Ala Arg Pro Ser Glu
```

```
                      485                 490                 495
Thr Thr Leu Cys Gln Val Ala Gly Trp Gly His Gln Phe Glu Gly Ala
                500                 505                 510

Glu Glu Tyr Ala Ser Phe Leu Gln Glu Ala Gln Val Pro Phe Leu Ser
            515                 520                 525

Leu Glu Arg Cys Ser Ala Pro Asp Val His Gly Ser Ser Ile Leu Pro
        530                 535                 540

Gly Met Leu Cys Ala Gly Phe Leu Glu Gly Gly Thr Asp Ala Cys Gln
545                 550                 555                 560

Gly Asp Ser Gly Gly Pro Leu Val Cys Glu Asp Gln Ala Ala Glu Arg
                565                 570                 575

Arg Leu Thr Leu Gln Gly Ile Ile Ser Trp Gly Ser Gly Cys Gly Asp
            580                 585                 590

Arg Asn Lys Pro Gly Val Tyr Thr Asp Val Ala Tyr Tyr Leu Ala Trp
        595                 600                 605

Ile Arg Glu His Thr Val Ser
            610                 615

<210> SEQ ID NO 23
<211> LENGTH: 609
<212> TYPE: PRT
<213> ORGANISM: Homo sapiens

<400> SEQUENCE: 23

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240
```

```
Ala Arg Leu Ser Gln Arg Phe Pro Lys Ala Glu Phe Ala Glu Val Ser
            245                 250                 255
Lys Leu Val Thr Asp Leu Thr Lys Val His Thr Glu Cys Cys His Gly
        260                 265                 270
Asp Leu Leu Glu Cys Ala Asp Asp Arg Ala Asp Leu Ala Lys Tyr Ile
        275                 280                 285
Cys Glu Asn Gln Asp Ser Ile Ser Ser Lys Leu Lys Glu Cys Cys Glu
        290                 295                 300
Lys Pro Leu Leu Glu Lys Ser His Cys Ile Ala Glu Val Glu Asn Asp
305                 310                 315                 320
Glu Met Pro Ala Asp Leu Pro Ser Leu Ala Ala Asp Phe Val Glu Ser
                325                 330                 335
Lys Asp Val Cys Lys Asn Tyr Ala Glu Ala Lys Asp Val Phe Leu Gly
                340                 345                 350
Met Phe Leu Tyr Glu Tyr Ala Arg Arg His Pro Asp Tyr Ser Val Val
            355                 360                 365
Leu Leu Leu Arg Leu Ala Lys Thr Tyr Glu Thr Thr Leu Glu Lys Cys
        370                 375                 380
Cys Ala Ala Ala Asp Pro His Glu Cys Tyr Ala Lys Val Phe Asp Glu
385                 390                 395                 400
Phe Lys Pro Leu Val Glu Glu Pro Gln Asn Leu Ile Lys Gln Asn Cys
                405                 410                 415
Glu Leu Phe Glu Gln Leu Gly Glu Tyr Lys Phe Gln Asn Ala Leu Leu
            420                 425                 430
Val Arg Tyr Thr Lys Lys Val Pro Gln Val Ser Thr Pro Thr Leu Val
        435                 440                 445
Glu Val Ser Arg Asn Leu Gly Lys Val Gly Ser Lys Cys Cys Lys His
    450                 455                 460
Pro Glu Ala Lys Arg Met Pro Cys Ala Glu Asp Tyr Leu Ser Val Val
465                 470                 475                 480
Leu Asn Gln Leu Cys Val Leu His Glu Lys Thr Pro Val Ser Asp Arg
                485                 490                 495
Val Thr Lys Cys Cys Thr Glu Ser Leu Val Asn Arg Arg Pro Cys Phe
                500                 505                 510
Ser Ala Leu Glu Val Asp Glu Thr Tyr Val Pro Lys Glu Phe Asn Ala
            515                 520                 525
Glu Thr Phe Thr Phe His Ala Asp Ile Cys Thr Leu Ser Glu Lys Glu
        530                 535                 540
Arg Gln Ile Lys Lys Gln Thr Ala Leu Val Glu Leu Val Lys His Lys
545                 550                 555                 560
Pro Lys Ala Thr Lys Glu Gln Leu Lys Ala Val Met Asp Asp Phe Ala
                565                 570                 575
Ala Phe Val Glu Lys Cys Cys Lys Ala Asp Asp Lys Glu Thr Cys Phe
                580                 585                 590
Ala Glu Glu Gly Lys Lys Leu Val Ala Ala Ser Gln Ala Ala Leu Gly
            595                 600                 605
Leu

<210> SEQ ID NO 24
<211> LENGTH: 12
<212> TYPE: PRT
<213> ORGANISM: Artificial Sequence
<220> FEATURE:
<223> OTHER INFORMATION: amino acid sequence of an Infestin-4 variant
```

```
<400> SEQUENCE: 24

Val Arg Asn Pro Cys Ala Cys Phe Arg Asn Tyr Val
1               5                   10

<210> SEQ ID NO 25
<211> LENGTH: 12
<212> TYPE: PRT
<213> ORGANISM: Artificial Sequence
<220> FEATURE:
<223> OTHER INFORMATION: amino acid sequence of an Infestin-4 variant

<400> SEQUENCE: 25

Asp Ser Leu Gly Arg Glu Val Arg Asn Pro Cys Ala
1               5                   10
```